US009187545B2

(12) United States Patent
Szkudlinski et al.

(10) Patent No.: US 9,187,545 B2
(45) Date of Patent: Nov. 17, 2015

(54) GLYCOPROTEIN HORMONE LONG-ACTING SUPERAGONISTS

(71) Applicant: Trophogen Inc., Rockville, MD (US)

(72) Inventors: Mariusz Szkudlinski, Rockville, MD (US); Bruce D. Weintraub, Rockville, MD (US)

(73) Assignee: Trophogen, Inc., Rockville, MD (US)

( * ) Notice: Subject to any disclaimer, the term of this patent is extended or adjusted under 35 U.S.C. 154(b) by 0 days.

(21) Appl. No.: 13/954,690

(22) Filed: Jul. 30, 2013

(65) Prior Publication Data

US 2014/0031530 A1 Jan. 30, 2014

Related U.S. Application Data

(60) Provisional application No. 61/677,331, filed on Jul. 30, 2012.

(51) Int. Cl.
*C07K 14/59* (2006.01)

(52) U.S. Cl.
CPC .................................... *C07K 14/59* (2013.01)

(58) Field of Classification Search
None
See application file for complete search history.

(56) References Cited

U.S. PATENT DOCUMENTS

| | | | | |
|---|---|---|---|---|
| 6,361,992 | B1 | 3/2002 | Szkudlinski et al. | |
| 7,070,788 | B2 | 7/2006 | Szkudlinski et al. | |
| 7,112,341 | B1 * | 9/2006 | Nagarajan et al. | 424/499 |
| 7,687,610 | B2 | 3/2010 | Szkudlinski et al. | |
| 8,044,187 | B2 | 10/2011 | Szkudlinski et al. | |
| 8,377,879 | B2 | 2/2013 | Szkudlinski et al. | |
| 2002/0110909 | A1 | 8/2002 | Szkudlinski et al. | |
| 2002/0127652 | A1 | 9/2002 | Schambye et al. | |
| 2007/0219116 | A1 | 9/2007 | Szkudlinski et al. | |
| 2007/0298463 | A1 | 12/2007 | Shemesh et al. | |

FOREIGN PATENT DOCUMENTS

| | | |
|---|---|---|
| WO | WO 97/42322 | 11/1997 |
| WO | WO 2005/089445 | 9/2005 |
| WO | WO 2011/075606 | 6/2011 |
| WO | WO 2014/022283 | 2/2014 |

OTHER PUBLICATIONS

Heikoop et al., *Towards minimized gonadotropins with full bioactivity*, 261 Eur. J. Biochem. 81-83 (1999).
Legardinier et al., *Stability and biological activities of heterodimeric and single-chain equine LH/chorionic gonadotropin variants*, 40 Journal of Molecular Endocrinology 185-198 (2008).
International Search Report dated Feb. 10, 2014, in corresponding PCT/US13/52510.
Combarnous, *Molecular Basis of the Specificity of Binding of Glycoprotein Hormones to Their Receptors*, 13(4) Endocrine Reviews 670-691 (1992).
Dias et al., *Structural Biology of Human Follitropin and Its Receptor*, 32 Archives of Medical Research 510-519 (2001).
Mueller et al., *The hinge region: an important receptor component for GPHR function*, 21(2) Trends in Endocrinology and Metabolism 111-122 (Oct. 12, 2009).
Mueller et al., *Identification of Novel TSH Interaction Sites by Systematic Binding Analysis of the TSHR Hinge Region*, 152(8) Endocrinology 3268-3278 (Aug. 2011).
Mueller et al., *The Superagonistic Activity of Bovine Thyroid-stimulating Hormone (TSH) and the Human TR1401 TSH Analog Is Determined by Specific Amino Acids in the Hinge Region of The Human TSH Receptor*, 284(24) The Journal of Biological Chemistry 16317-16324 (Jun. 12, 2009).
Murphy et al., *Equine Chorionic Gonadotropin*, 12(1) Endocrine Reviews 27-44 (1991).
Perlman et al., *Glycosylation of an N-Terminal Extension Prolongs the Half-Life and Increases in* in Vivo *Activity of Follicle Stimulating Hormone*, 88(7) The Journal of Clinical Endocrinology & Metabolism 3227-3235 (2003).
Szkudliniski et al., *Engineering human glycoprotein hormone superactive analogues*, 14 Nature Biotechnology 1257-1263 (Oct. 1996).
Szkudlinski et al., *Thyroid-Stimulating Hormone and Thyroid-Stimulating Hormone Receptor Structure-Function Relationships*, 82 Physiol. Rev. 473-502 (2002).
Trousdale et al., *Efficacy of native and hyperglycosylated follicle stimulating hormone analogues for promoting fertility in female mice*, 91(1) Fertil. Steril. 265-2470 (Nov. 13, 2007).
*Alignment between the bovine and human gonadotropin alpha subunit is provided*, website: blast.ncbi.nlm.nih.gov/Blast.cgi (downloaded on Jan. 25, 2012).

* cited by examiner

*Primary Examiner* — Michael Pak
(74) *Attorney, Agent, or Firm* — Buchanan Ingersoll & Rooney PC

(57) ABSTRACT

This invention provides long-acting, superactive analogs of glycoprotein hormones demonstrating enhanced bioactivity both in vitro and in vivo as compared to wild type counterparts. The analogs are particularly useful for treating subjects showing low receptor expression or poor receptor responsiveness, and for the treatment of any condition associated with glycoprotein hormone activity.

14 Claims, 12 Drawing Sheets

A.

B.

| | EC50 (ng/ml) | Top of the curve (Vmax) (pmoles cAMP/ml) |
|---|---|---|
| A2 | 16.22 | 133.1 |
| Insert 2 | 5.28 | 177.9 |
| 5R | 2.45 | 176.7 |

A.

B.

GLYCOPROTEIN HORMONE LONG-ACTING SUPERAGONISTS

SEQUENCE LISTING INFORMATION

A computer readable text file, entitled "056815-5010-SequenceListing.txt," created on or about Nov. 20, 2013 with a file size of about 30 kb contains the sequence listing for this application and is hereby incorporated by reference in its entirety.

FIELD OF INVENTION

This invention relates generally to modified glycoprotein hormones having superagonist activity, and the use thereof in the treatment of conditions associated with glycoprotein hormone activity. More specifically, this invention relates to modified glycoprotein molecules containing amino acid substitutions and one or more inserted peptides in the alpha subunit as compared to wild type alpha subunit, wherein such modified molecules exhibit enhanced pharmacological properties as compared to wild type glycoproteins.

BACKGROUND OF INVENTION

The gonadotropins follitropin (follicle-stimulating hormone, FSH) and chorionic gonadotropin, (CG), lutropin (luteinizing hormone, LH), and thyrotropin (thyroid-stimulating hormone, TSH) comprise the family of glycoprotein hormones. Each hormone is a heterodimer of two non-covalently linked subunits: alpha and beta. Within the same species, the amino acid sequence of the alpha-subunit is identical in all the hormones, whereas the sequence of the beta-subunit is hormone specific (Pierce, Ann. Rev. Biochem. 50:465-495 (1981)). The fact that the sequences of the subunits are highly conserved from fish to mammals implies that these hormones have evolved from a common ancestral protein (Fontaine, Gen. Comp. Endocrinol. 32:341-347 (1977)).

Previous studies with modified glycoprotein hormones have revealed encouraging data. For example, in addition to providing modified glycoprotein hormones with increased activity, further mutations have demonstrated an increase in receptor affinity binding (see e.g. WO 2005/089445 and WO 2005/101000). However, while affinity was increased, studies demonstrated that modified glycoprotein hormones were cleared as quickly if not faster than their wild type counterparts. In order to generate a clinically useful superagonist with enhanced activity, modified glycoprotein superagonist should have an improved biological half-life in addition to improved receptor binding affinity. However, previous attempts to further modify glycoprotein hormones to increase half-life and improve bioavailability have been less than satisfactory and instead the modified glycoprotein hormones demonstrated only an attenuated response.

SUMMARY OF INVENTION

The invention encompasses a modified glycoprotein hormone comprising an amino acid sequence with at least one conservative basic amino acid substitution at Q13, E14, P16 or Q20 and an insert of VNVTINVT (SEQ ID NO: 20) between D3 and Q5 of the alpha subunit of a glycoprotein hormone.

In some embodiments, the modified glycoprotein hormone comprises at least two or at least three basic amino acid substitutions at Q13, P16 and Q20. In some embodiments, the modified glycoprotein hormone further comprises a basic amino acid substitution at E14. In some embodiments, the basic amino acid is arginine.

In some embodiments, the alpha subunit comprises an amino acid sequence with at least 85% identity to SEQ ID NO: 11 and further comprises the beta subunit of leutenizing hormone (LH), chorionic gonadotropin (CG), follicle-stimulating hormone (FSH) or thyroid-stimulating hormone (TSH). In some embodiments, the alpha subunit is derived from a human alpha subunit (SEQ ID NO: 6).

The invention encompasses a modified glycoprotein hormone comprising an amino acid sequence with at least one conservative basic amino acid substitution at K15, K17, K20 or K24 and an insert of NVTINV (SEQ ID NO: 1) between F6 and T7 of the alpha subunit of a glycoprotein hormone.

In some embodiments, modified glycoprotein hormone comprises at least two, or at least three, or at least four basic amino acid substitutions at K15, K17, K20 and K24. In some embodiments, the modified glycoprotein hormone further comprises a basic amino acid substitution at E18. In some embodiments, the basic amino acid is arginine.

In some embodiments, the alpha subunit comprises an amino acid sequence with at least 85% identity to SEQ ID NO: 7 and further comprises the beta subunit of leutenizing hormone (LH), chorionic gonadotropin (CG), follicle-stimulating hormone (FSH) or thyroid-stimulating hormone (TSH). In some embodiments, the alpha subunit is derived from a bovine, porcine, or ovine alpha subunit (SEQ ID NO: 2, SEQ ID NO: 5, SEQ ID NO: 3, respectively).

The invention encompasses a modified glycoprotein hormone comprising an amino acid sequence with at least one conservative basic amino acid substitution at K15, E18, K20 or K24 and an insert of NVTINV (SEQ ID NO: 1) between F6 and T7 or alternatively an insert of NV between F6 and T7 plus an insert of INV between T7 and T8 of the alpha subunit of a glycoprotein hormone.

In some embodiments, modified glycoprotein hormone comprises at least two, or at least three, or at least four basic amino acid substitutions at K15, E18, K20 and K24. In some embodiments, the modified glycoprotein hormone includes an insert of NVTINV (SEQ ID NO: 1) between F6 and T7 of the alpha subunit. In some embodiments, the modified glycoprotein hormone includes an insert of NV between F6 and T7 plus an insert of INV between T7 and T8 of the alpha subunit. In some embodiments, the basic amino acid is arginine of histidine. In some embodiments, the basic amino acid is arginine.

In some embodiments, the alpha subunit comprises an amino acid sequence with at least 85% identity to SEQ ID NO: 4 and further comprises the beta subunit of leutenizing hormone (LH), chorionic gonadotropin (CG), follicle-stimulating hormone (FSH) or thyroid-stimulating hormone (TSH). In some embodiments, the alpha subunit is derived from an equine alpha subunit (SEQ ID NO: 4).

The invention also encompasses a method for stimulating a glycoprotein receptor in an animal, comprising administering of the above modified glycoprotein hormones to the animal. The invention also encompasses a method for stimulating ovulation in an animal comprising administering any of the above the modified glycoprotein hormones to the animal. In some embodiments the animal is a human, cow, sheep, pig or horse.

BRIEF DESCRIPTION OF THE DRAWINGS

FIG. 1A shows a comparison of Folltropin®-V (pFSH), bFSH-WT (wild-type) with bFSH-5R analog. FIG. 1B shows attenuation of the in vitro bioactivity of hFSH-TR4402 analog (Transient 4402) by two N-terminal extensions (ANITV, NITV) and one internal neoglycosylation (V78N) (SPA cAMP assay). FIG. 1C shows a comparison of bFSH-5R analog with the Insert 1 (5R+Insert 1) and Insert 2 (5R+Insert2).

FIG. 3A illustrates charge heterogeneity analysis using IEF followed by Western blot. Suboptimal sialylation of Lot 3 (Lanes 2 and 3) is in sharp contrast with optimal highly acidic isoforms detected in Lot 4 (Lanes 5 and 6). Lane 1, IEF 3-10 marker; Lane 2, TR55601/Lot 3 (8 μg); Lane 3, TR55601/Lot 3 (4 μg); Lane 4 and 8, TR4401 (1 μg); Lane 5, TR55601/Lot 4 (8 μg); Lane 6, TR55601/Lot 4 (4 μg); Lane 8, IEF 3-10 marker. FIG. 3B illustrates Analysis of charged isoforms using neuraminidase (*Vibrio cholerae*), IEF and Western blot. Untreated TR55601/Lot 4 sample (Lanes 2 and 3) and TR55601/Lot 4 sample treated with neuraminidase before applying to 3-10 IEF gel (Lanes 4-6). Lane 1, IEF 3-10 marker; Lane 2, untreated TR55601/Lot 4 (8 μg); Lane 3, untreated TR55601/Lot 4 (4 μg); Lane 4, treated TR55601/Lot 4 (4 μg); Lane 5, treated TR55601/Lot 4 (2 μg); Lane 6, treated TR55601/Lot 4 (1 μg). The IEF profile for the neuraminidase digested isoforms has shifted to the pI range from 7.8 to 10.0. The average shift of pI is about 5 pH units and multiple bands (close to 10 bands) transformed into one major band (pI~9.5) and three minor bands (pI 7.8-10.0), indicating that the majority of the observed charge heterogeneity (FIG. 3A—Lot 4) is dependent on terminal sialic acid residues with a minor component of other modifications such as deamidation and/or proteolytic degradation. The residual basic bands (pI 4.8-5.5) shown in 3B are nonspecific, derived from neuraminidase preparation. FIG. 3C shows the analysis of charged isoforms of TR55601-Lot 5 by IEF 3-10 in pI gradient gel (IEF 3-10) followed by Western blotting. Lane 1, IEF 3-10 marker; Lane 2, TR55601-Lot 5 (4 μg); Lane 3, TR55601-Lot 5 (4 μg); Lane 4, TR55601-Lot 4 (4 μg); Lane 5, TR55601-Lot 4 (8 μg); Lane 6, TR55601-Lot 3 (4 μg); lane 7, TR55601-Lot 3 (8 μg). FIG. 3D illustrates SDS-Western Blot analysis of TR55601Lot 5 compared to TR55601Lot 4 and Fol-V. Lane 1, protein marker; Lane 2: Lot 4, 500 ng; Lane 3: Lot 5, 1 ul; Lane 4: empty lane; Lane 5: Lot 4, 4 ug; Lane 6: Lot 5, 15 ul; Lane 7: Fol-V, 673 ng; Lane 8: protein marker.

DETAILED DESCRIPTION OF THE INVENTION

Figure 1:
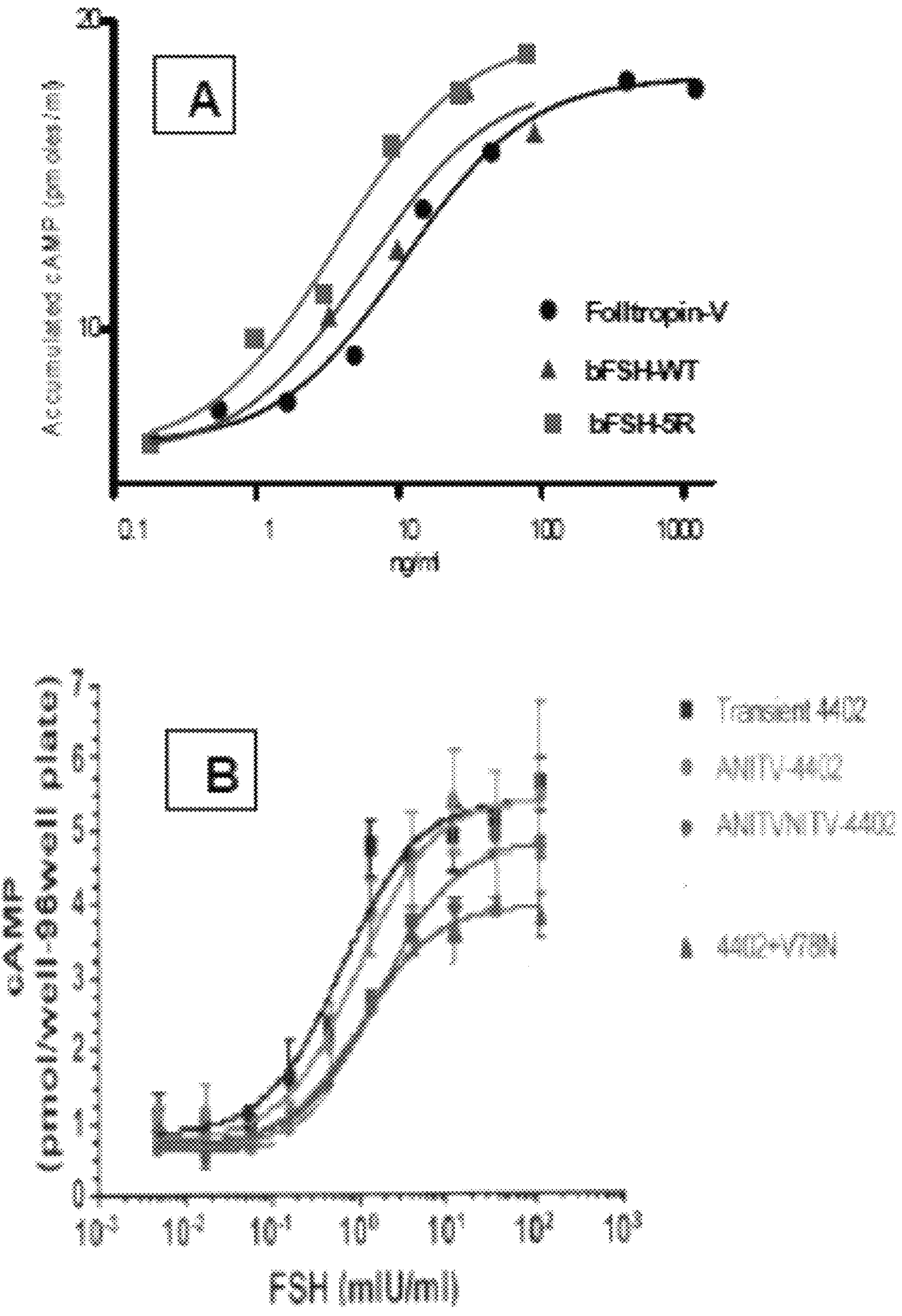
FIG. 1 shows cAMP stimulation in CHO-FSHR cells with selected bFSH analogs produced by transient transfection.
Figure 1:
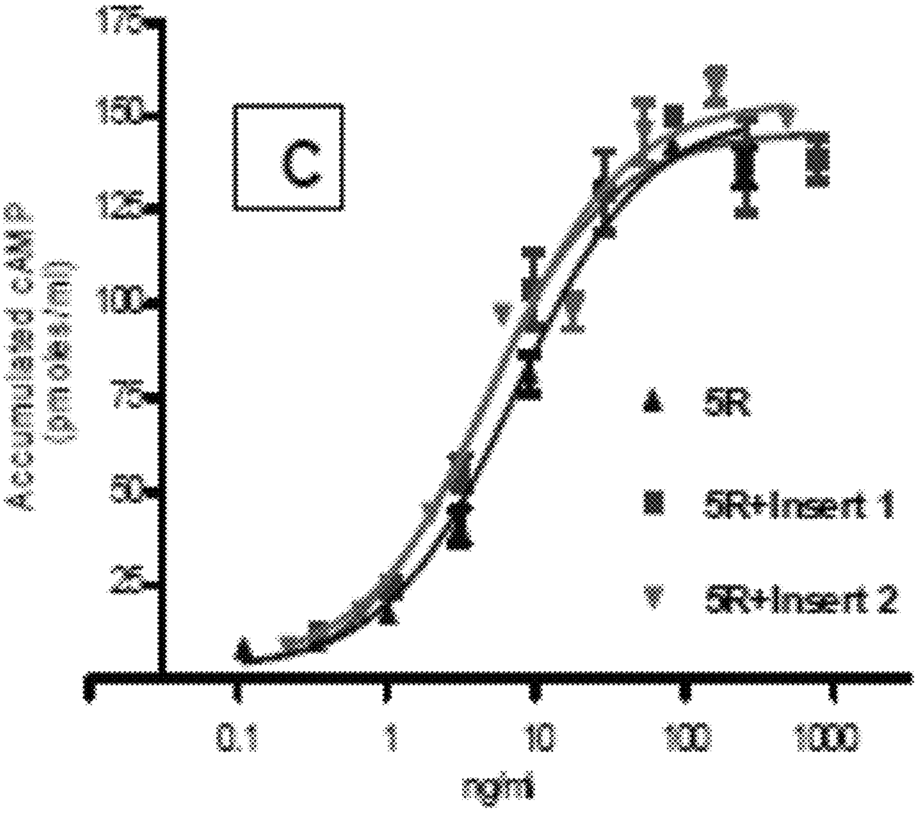

The present invention provides modified superactive glycoprotein hormone molecules showing surprisingly enhanced potency and increased biological half-life as compared to their wild type counterparts. Being modified means that, while the protein contains an amino acid sequence which differs from the wild-type glycoprotein hormones, the sequence has been changed such that it is not identical to the known glycoprotein hormones sequence of another species. Superactivity may be assessed according to a variety of parameters, including potency and efficacy. Potency is a parameter of bioactivity that is determined by measuring the half maximal response. Differences in potency are determined by comparing the value of the glycoprotein hormones response of the analog halfway between baseline and maximum ($EC_{50}$) versus that of wild type glycoprotein hormones. Glycoprotein hormone responses may be measured in vitro using purified proteins, or may be estimated following transient transfection of a nucleic acid encoding the modified protein. Glycoprotein hormone responses may also be measured in vivo, i.e. in an animal responsive to said glycoprotein hormone analog. Such responses encompass any known cellular or biological and quantitative or qualitative response of glycoprotein hormone binding to its receptor, e.g. cAMP production, synthesis of proteins such as progesterone, fertilization rate, blastocyst formation rate, embryo development per fertilized oocyte, etc. Efficacy (Vmax) or maximum response is another parameter of bioactivity. As discussed herein, parameters of bioactivity may vary depending on receptor number and receptor coupling in the assay cell line. In systems with lower receptor numbers or impaired coupling, differences are more discernable in terms of Vmax (efficacy). In systems where receptors are overexpressed, differences in potency are more visible.

For example, in instances where the modified glycoprotein hormone is a modified FSH or CG molecule, in vivo quantitative and qualitative parameters such as quantity of oocytes, fertilization rate and blastocyst and embryo formation rates may be measured at the maximally effective dose for oocyte number. The maximally effective dose for oocyte number is the optimal amount of superactive FSH for both oocyte quality and quantity. The maximally effective dose for oocyte number is dependent on an animal's weight and rate of metabolism. For example, the maximally effective dose for a larger animal with a slower rate of metabolism is greater than the maximally effective dose for a smaller animal with a higher rate of metabolism. The maximally effective dose is determined empirically for each animal.

However, regardless of the system used, the modified superactive glycoprotein hormone proteins of the invention may demonstrate at least about a 2 to 10 fold increase in potency or at least about a 20-fold, 30-fold, 40-fold, 50-fold, 60-fold, 70-fold, 80-fold, 90-fold or even 100-fold increase in potency compared to a wild type counterpart, or about a 2 to 10% increase in maximal efficacy, or at least a 20%, 30%, 40%, 50%, 60%, 70%, 80%, 90%, or even 100% increase in maximal efficacy compared to a wild type counterpart. The superactive analogs of the invention may also provide about a five to ten fold increase in potency or 5% to 10% increase in maximal efficacy as compared to wild type FSH. Some of the modified proteins of the invention may demonstrate at least about a thirty to fifty fold increase in potency or 30% to 50% increase in maximal efficacy as compared to wild type. Thus, the modified glycoprotein hormone proteins of the present invention may be useful for treating subjects with low receptor number or deficiencies in receptor response, since the modified proteins of the invention may maintain at least a 10 fold increase in potency or 10% increase in maximal efficacy even in systems with low receptor number or response.

The rate of absorption of a modified superactive glycoprotein hormone may result in increased duration of action. A modified glycoprotein hormone analog with a decreased rate of absorption and increased duration of action may be beneficial for hyposensitive subjects, such as those suffering from fertility disorders. The rate of absorption is measured by $K_a$. The rate of elimination is measured by $K_e$.

The modified glycoprotein hormone molecules of the invention include modified proteins of species selected from the group consisting of human, bovine, equine, porcine, ovine, murine, rat, rabbit, primate, etc. Fish glycoprotein hormone (also known as GTH-1) may be used in aquaculture, i.e., in order to assist growth of endangered or other fish species in captivity. Other species of modified glycoprotein hormones may be used in agricultural breeding, and further in a laboratory setting for testing the effects of different combined mutations on various male and female glycoprotein hormone-related conditions.

Figure 4:
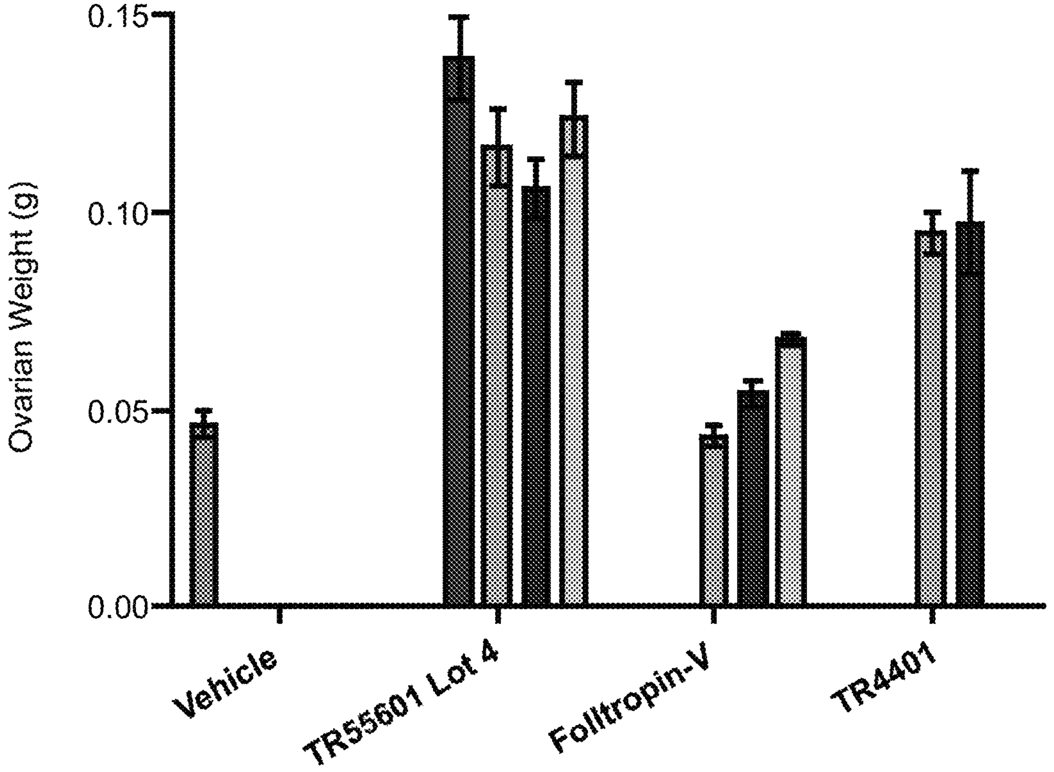
FIG. 4 shows the results from Classic Steelman-Pohley bioassay with hCG augmentation of ovarian weight in immature (22 days old) Sprague-Dawley female rats. Ovarian weights were measured 72 hours after dosing. Data are presented as average total ovarian weight of two ovaries+SEM (n=5 per dose, per group). Rats were stimulated with one single injection of test article or vehicle, supplemented with 40 IU of hCG. The following dosage groups were used: Group 1 was receiving hCG only (no FSH), Groups 2-5 were receiving TR55601Lot 4 (0.33 μg, 1.0 μg, 3.33 μg, and 10 μg, respectively from left to right), Groups 6-8 were receiving Folltropin-V® (3,333 μg, 10,000 mg, and 30,000 μg respectively from left to right), and Group 9-10 was receiving TR4401 (1.0 mg and 3.33 μg).

The modified glycoprotein hormone molecules of other species have substitutions at positions corresponding to those in the modified human (e.g. FIG. 12), bovine (see FIG. 4), ovine, equine and porcine glycoprotein hormone molecules disclosed herein, which may be identified using any alignment program, including but not limited to DNASIS, ALIONment, SIM and GCG programs such as Gap, BestFit, FrameAlign and Compare.

Modified glycoprotein hormone molecules of the present invention comprise at least a modified alpha-subunit, wherein the alpha subunit comprises at least two basic amino acids such at lysine residues. In human alpha subunits, the basic amino acids may be introduced at positions 13, 14, 16 and 20 of wild type human alpha subunit (SEQ ID NO: 6). In other species, the basic amino acids may be introduced at positions corresponding to positions 15, 17, 20 and 24 of wild type bovine alpha (SEQ ID NO: 2), wild type porcine alpha (SEQ ID NO: 5) and wild type ovine alpha (SEQ ID NO: 3), and positions 15, 20 and 24 of wild type equine alpha (SEQ ID NO: 4). The glutamate residue at position 18 (bovine, porcine, ovine and equine) may also be substituted with a basic amino acid. In some embodiments, the basic amino acid may be arginine or histidine. In some embodiments, the basic amino acid may be arginine.

A peptide with the sequence NVTINV (SEQ ID NO: 1) or TNVTINV (SEQ ID NO: 12) or VNVTINVT (SEQ ID NO: 20) may be inserted between amino acids D3 and Q5 of the human alpha subunit (SEQ ID NO: 6) and between F6 and T7 of the bovine, porcine, ovine and equine alpha subunits. Alternatively, modified glycoprotein hormone alpha subunit of bovine, porcine, ovine or euqine may include an insert of NV between F6 and T7 plus an insert of INV between T7 and T8. The modified proteins of the invention may also contain further substitutions, particularly conservative substitutions that do not alter the enhanced properties of the protein. Typically, however, such modified proteins will contain less than five substitutions at positions other than those listed above, and may exhibit complete amino acid sequence identity with the corresponding wild-type glycoprotein hormone alpha in positions other than the positions listed above.

Basic amino acids comprise the amino acids lysine, arginine, and histidine, and any other basic amino acid which may be a modification to any of these three amino acids, synthetic basic amino acids not normally found in nature, or any other amino acid which is positively charged at a neutral pH. The basic amino acids, among others, are selected from the group consisting of lysine and arginine.

Exemplary modified alpha molecules having the basic amino acid substitutions and the peptide insert are set forth in SEQ ID NO: 11 (human), SEQ ID NO: 7 (bovine), SEQ ID NO: 8 (ovine), SEQ ID NO: 10 (porcine), and SEQ ID NO: 9 (equine). The present invention provides for modified glycoproteins with amino acid sequences with at least 80%, 85%, 86%, 87%, 88%, 89%, 90%, 91%, 92%, 93%, 94%, 95%, 96%, 97%, 98%, 99% or higher identity with any of SEQ ID NO: 7 to 11.

The modified alpha subunits of the modified glycoprotein hormone proteins of the invention may also have an alpha subunit comprising two, three, four or five basic amino acid substitutions. The substituted amino acids may be lysine residues, glutamate residues, proline residues or glutamine residues. For example, in wild type bovine alpha subunits, one or more of the lysines at positions 15, 17, 20 and 24 may be substituted, as well as the glutamate at position 18 with a basic amino acid, such as an arginine and a histidine. In wild type human alpha subunits, one or more of the glutamines at positions 13 and 20 may be substituted, as well as the glutamate at position 14 and the proline at position 16 with a basic amino acid, such as an arginine and a histidine. In wild type porcine alpha subunits, one or more of the lysines at positions 15, 17, 20 and 24 may be substituted, as well as the glutamate at position 18 with a basic amino acid, such as an arginine and a histidine. In wild type ovine alpha subunits, one or more of the lysines at positions 15, 17, 20 and 24 may be substituted, as well as the glutamate at position 18 with a basic amino acid, such as an arginine and a histidine. In wild type equine alpha subunits, one or more of the lysines at positions 15, 20 and 24 may be substituted, as well as the glutamate at position 18 with a basic amino acid, such as an arginine and a histidine.

By way of example, further modified bovine alpha subunits are presented in the sequences as set forth in SEQ ID NO: 14 to 19 and 22. The present invention provides for modified glycoproteins with amino acid sequences with at least 85%, 86%, 87%, 88%, 89%, 90%, 91%, 92%, 93%, 94%, 95%, 96%, 97%, 98%, 99% or higher identity with any of SEQ ID NO: 14 to 19 and 22.

By way of example, further modified equine alpha subunits are presented in the sequences as set forth in SEQ ID NO: 38 to 42. The present invention provides for modified glycoproteins with amino acid sequences with at least 85%, 86%, 87%, 88%, 89%, 90%, 91%, 92%, 93%, 94%, 95%, 96%, 97%, 98%, 99% or higher identity with any of SEQ ID NO: 43 to 45.

Further modified alpha subunits may be designed by comparing the amino acid sequences of the alpha subunit of interest to that of other species to identify the corresponding basic residues in the proteins of other species. Such methods are disclosed in U.S. Pat. No. 6,361,992 which is herein incorporated by reference in its entirety. Consideration may also be given to the relative biological activity of the glycoprotein hormone from various species as to which species to choose for comparison and substitution. Further, homology modeling based on the structure of related glycoprotein hormones is useful to identify surface-exposed amino acid residues. To modify additional amino acid positions, glycoprotein hormone sequences from human and non-humans can be aligned using standard computer software programs such as DNASIS (Hitachi Software Engineering) or any of the other alignment programs listed above, including but not limited to ALIONment, SIM and GCG programs such as Gap, BestFit, FrameAlign and Compare. The amino acid residues that differ between the human and the non-human glycoprotein hormone can then be substituted using one of the above-mentioned techniques, and the resultant glycoprotein hormone assayed for its potency using one of the herein-mentioned assays.

Accordingly, the present invention also provides a modified FSH protein having increased potency over a wild-type FSH from the same species comprising the modified alpha subunits described herein.

The present invention also provides a modified LH protein having increased potency over a wild-type LH from the same species comprising the modified alpha subunits described herein.

The present invention also provides a modified TSH protein having increased potency over a wild-type TSH from the same species comprising the modified alpha subunits described herein.

The present invention also provides a modified CG protein having increased potency over a wild-type CG from the same species comprising the modified alpha subunits described herein.

The present invention also encompasses fragments of the analogs described herein that have either superagonist or antagonist activity. For example, fragments of the modified alpha chains of the invention may be used either alone or in combination with either a fragment or full length beta chain to create superagonist compounds. In some cases, fragments of the modified alpha subunit molecules of the invention may also be used as antagonists, for instance, to limit the duration of activity of an glycoprotein hormone therapeutic after it has been administered.

The present invention also provides for nucleic acid sequences encoding the modified glycoprotein hormones described herein. The present invention also provides nucleic acids that encode polypeptides with conservative amino acid substitutions. The nucleic acids of the present invention may encode polypeptides that transport sugar. The isolated nucleic acids may have at least about 30%, 40%, 50%, 60%, 70%, 80% 85%, 90%, 95%, or 99% sequence identity with the above identified sequences. The isolated nucleic acids may encode a polypeptide having an amino acid sequence having at least about 30%, 40%, 50%, 60%, 70%, 80%, 85%, 90%, 95%, or 99% sequence identity to amino acid sequences encoded by the above identified accession numbers. The isolated nucleic acid encoding a transporter may hybridize to the above identified nucleic acid sequences.

The nucleic acid encoding the modified glycoprotein hormone proteins may be genetically fused to expression control sequences for expression. Suitable expression control sequences include promoters that are applicable in the target host organism. Such promoters are well known to the person skilled in the art for diverse hosts from prokaryotic and eukaryotic organisms and are described in the literature. For example, such promoters may be isolated from naturally occurring genes or may be synthetic or chimeric promoters.

The present invention also provides expression cassettes for inserting the nucleic acid encoding a modified glycoprotein hormone protein into target nucleic acid molecules such as vectors. For this purpose, the expression cassette is provided with nucleotide sequences at the 5'- and 3'-flanks to facilitate removal from and insertion into specific sequence positions like, for instance, restriction enzyme recognition sites or target sequences for homologous recombination as, e.g. catalyzed by recombinases. In addition to the nucleic acid molecule or expression cassette of the invention, the vector may contain further genes such as marker genes which allow for the selection of said vector in a suitable host cell and under suitable conditions. Generally, the vector also contains one or more origins of replication. The vectors may also comprise terminator sequences to limit the length of transcription beyond the nucleic acid encoding the transporters of the present invention.

Advantageously, the nucleic acid molecules contained in the vectors are operably linked to expression control sequences allowing expression, i.e. ensuring transcription and synthesis of a translatable RNA, in prokaryotic or eukaryotic cells.

The term isolated refers to molecules separated from other cell/tissue constituents (e.g. DNA or RNA), that are present in the natural source of the macromolecule. The term isolated as used herein also refers to a nucleic acid or peptide that is substantially free of cellular material, viral material, and culture medium when produced by recombinant DNA techniques, or that is substantially free of chemical precursors or other chemicals when chemically synthesized. Moreover, an isolated nucleic acid or peptide may include nucleic acid or peptide fragments which are not naturally occurring as fragments and would not be found in the natural state.

The terms plasmid and vector are used interchangeably as the plasmid is the most commonly used form of vector. However, the invention is intended to include such other forms of expression vectors which serve equivalent functions and which become known in the art subsequently hereto. A vector may be any of a number of nucleic acids into which a desired sequence may be inserted by restriction and ligation for transport between different genetic environments or for expression in a host cell. Vectors are typically composed of DNA, although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

Vectors may further contain a promoter sequence. A promoter may include an untranslated nucleic acid sequence usually located upstream of the coding region that contains the site for initiating transcription of the nucleic acid. The promoter region may also include other elements that act as regulators of gene expression. In further embodiments of the invention, the expression vector contains an additional region to aid in selection of cells that have the expression vector incorporated. The promoter sequence is often bounded (inclusively) at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain TATA boxes and CAT boxes. Activation of promoters may be specific to certain cells or tissues, for example by transcription factors only expressed in certain tissues, or the promoter may be ubiquitous and capable of expression in most cells or tissues.

Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Vectors may be those capable of autonomous replication and expression of the structural gene products present in the DNA segments to which they are operably joined. An expression vector is one into which a desired nucleic acid sequence may be inserted by restriction and ligation such that it is operably joined or operably linked to regulatory sequences and may be expressed as an RNA transcript. Expression refers to the transcription and/or translation of an endogenous gene, transgene or coding region in a cell.

A coding sequence and a regulatory sequence are operably joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

Some aspects of the present invention include the transformation and/or transfection of nucleic acids. Transformation is the introduction of exogenous or heterologous nucleic acid to the interior of a prokaryotic cell. Transfection is the introduction of exogenous or heterologous nucleic acid to the interior of a eukaryotic cell. The transforming or transfecting nucleic acid may or may not be integrated (covalently linked) into chromosomal DNA making up the genome of the cell. In prokaryotes, for example, the transforming nucleic acid may be maintained on an episomal element such as a plasmid or viral vector. With respect to eukaryotic cells, a stably transfected cell is one in which the transfecting nucleic acid has become integrated into a chromosome so that it is inherited by daughter cells through chromosome replication. This stability is demonstrated by the ability of the eukaryotic cell to establish cell lines or clones comprised of a population of daughter cells containing the transfected nucleic acid.

There are numerous *E. coli* (*Escherichia coli*) expression vectors known to one of ordinary skill in the art which are useful for the expression of the nucleic acid insert. Other microbial hosts suitable for use include bacilli, such as *Bacillus subtilis*, and other enterobacteriaceae, such as *Salmonella, Serratia*, and various *Pseudomonas* species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary, an amino terminal methionine can be provided by insertion of a Met codon 5' and in-frame with the downstream nucleic acid insert. Also, the carboxyl-terminal extension of the nucleic acid insert can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MF"-1 gene) is routinely used to direct protein secretion from yeast. (Brake, Proc. Nat. Acad. Sci., 81:4642-4646 (1984)). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage signal sequence. The FSH coding sequence can be fused in-frame to the pre-pro-alpha-factor leader region. This construct is then put under the control of a strong transcription promoter, such as the alcohol dehydrogenase I promoter or a glycolytic promoter. The nucleic acid coding sequence is followed by a translation termination codon which is followed by transcription termination signals. Alternatively, the nucleic acid coding sequences can be fused to a second protein coding sequence, such as Sj26 or beta.-galactosidase, which may be used to facilitate purification of the fusion protein by affinity chromatography. The insertion of protease cleavage sites to separate the components of the fusion protein is applicable to constructs used for expression in yeast. Efficient post-translational glycosylation and expression of recombinant proteins can also be achieved in Baculovirus systems.

Mammalian cells permit the expression of proteins in an environment that favors important post-translational modifications such as folding and cysteine pairing, addition of complex carbohydrate structures, and secretion of active protein. Vectors useful for the expression of active proteins in mammalian cells are characterized by insertion of the protein coding sequence between a strong viral promoter and a polyadenylation signal. The vectors can contain genes conferring hygromycin resistance, gentamicin resistance, or other genes or phenotypes suitable for use as selectable markers, or methotrexate resistance for gene amplification. The chimeric protein coding sequence can be introduced into a Chinese hamster ovary (CHO) cell line using a methotrexate resistance-encoding vector, or other cell lines using suitable selection markers. Presence of the vector DNA in transformed cells can be confirmed by Southern blot analysis. Production of RNA corresponding to the insert coding sequence can be confirmed by Northern blot analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Exemplary expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transformation is commonly utilized for prokaryotic cells, whereas calcium phosphate, DEAE dextran, or lipofectin mediated transfection or electroporation may be used for other cellular hosts.

Alternative vectors for the expression of genes in mammalian cells, those similar to those developed for the expression of human gamma-interferon, tissue plasminogen activator, clotting Factor VIII, hepatitis B virus surface antigen, protease Nexin1, and eosinophil major basic protein, can be employed. Further, the vector can include CMV promoter sequences and a polyadenylation signal available for expression of inserted nucleic acids in mammalian cells (such as COS-7).

Expression of the gene or hybrid gene can be by either in vivo or in vitro. In vivo synthesis comprises transforming prokaryotic or eukaryotic cells that can serve as host cells for the vector. Alternatively, expression of the gene can occur in an in vitro expression system. For example, in vitro transcription systems are commercially available which are routinely used to synthesize relatively large amounts of mRNA. In such in vitro transcription systems, the nucleic acid encoding the glycoprotein hormone would be cloned into an expression vector adjacent to a transcription promoter. For example, the Bluescript II cloning and expression vectors contain multiple cloning sites which are flanked by strong prokaryotic transcription promoters (Stratagene). Kits are available which contain all the necessary reagents for in vitro synthesis of an RNA from a DNA template such as the Bluescript vectors (Stratagene). RNA produced in vitro by a system such as this can then be translated in vitro to produce the desired glycoprotein hormone (Stratagene).

Another method of producing a glycoprotein hormone is to link two peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry (Applied Biosystems). One skilled in the art can readily appreciate that a peptide or polypeptide corresponding to a hybrid glycoprotein hormone can be synthesized by standard chemical reactions. For example, a peptide or polypeptide can be synthesized and not cleaved from its synthesis resin whereas the other fragment of a hybrid peptide can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form a hybrid peptide. (Grant, Synthetic Peptides: A User Guide, W.H. Freeman (1992) and Bodansky, Principles of Peptide Synthesis, Springer-Verlag (1993)). Alternatively, the peptide or polypeptide can by independently synthesized in vivo as described above. Once isolated, these independent peptides or polypeptides may be linked to form a glycoprotein hormone via similar peptide condensation reactions. For example, enzymatic or chemical ligation of cloned or synthetic peptide segments can allow relatively short peptide fragments to be joined to produce larger peptide fragments, polypeptides or whole protein domains (Abrahmsen, Biochemistry, 30:4151 (1991); Dawson, Science, 266:776-779 (1994)).

The modified glycoprotein hormones of the present invention can be recombinant proteins obtained by cloning nucleic acids encoding the polypeptide in an expression system capable of producing the polypeptide fragments thereof. For example, one can determine the active domain of a modified alpha subunit which, together with the beta subunit, can interact with a glycoprotein hormone receptor and cause a biological effect associated with the glycoprotein hormone. In one example, amino acids found to not contribute to either the activity or the binding specificity or affinity of the glycoprotein hormone can be deleted without a loss in the respective activity.

For example, amino or carboxyl-terminal amino acids can be sequentially removed from either the native or the modified glycoprotein hormone and the respective activity tested in one of many available assays described above. In another example, the modified proteins of the invention may have a portion of either amino terminal or carboxyl terminal amino acids, or even an internal region of the hormone, replaced with a polypeptide fragment or other moiety, such as biotin, which can facilitate in the purification of the modified glycoprotein hormone. For example, a modified glycoprotein can be fused to a maltose binding protein, through either peptide chemistry of cloning the respective nucleic acids encoding the two polypeptide fragments into an expression vector such that the expression of the coding region results in a hybrid polypeptide. The hybrid polypeptide can be affinity purified by passing it over an amylose affinity column, and the modified glycoprotein can then be separated from the maltose binding region by cleaving the hybrid polypeptide with the specific protease factor Xa.

Active fragments of the modified glycoprotein hormone molecules of the invention can also be synthesized directly or obtained by chemical or mechanical disruption of larger glycoprotein hormone. An active fragment is defined as an amino acid sequence of at least about 5 consecutive amino acids derived from the naturally occurring amino acid sequence, which has the relevant activity, e.g., binding or regulatory activity. The fragments, whether attached to other sequences or not, can also include insertions, deletions, substitutions, or other selected modifications of particular regions or specific amino acids residues, provided the activity of the peptide is not significantly altered or impaired compared to the modified glycoprotein hormone. These modifications can provide for some additional property, such as to remove/add amino acids capable of disulfide bonding, to increase its bio-longevity, etc. In any case, the peptide must possess a bioactive property, such as binding activity, regulation of binding at the binding domain, etc. Functional or active regions of the glycoprotein hormone may be identified by mutagenesis of a specific region of the hormone, followed by expression and testing of the expressed polypeptide. Such methods are readily apparent to a skilled practitioner in the art and can include site-specific mutagenesis of the nucleic acid encoding the receptor.

The present invention also encompasses fusion proteins and chimeric proteins comprising the mutations described herein, including for instance, fusions to the FSH glycoprotein. Such a fusion protein may be made by ligating the appropriate nucleic acid sequences encoding the desired amino acid sequences to each other by methods known in the art, in the proper coding frame, and expressing the fusion protein by any of the means described above. Alternatively, such a fusion protein may be made by protein synthesis techniques, for example, using a peptide synthesizer. The single chain analogs and chimeric proteins of the invention may incorporate a peptide linker between the alpha and beta subunits, or between different portions of the chimeric protein.

Characterization of Glycoprotein Hormone Superagonists

The effect of the modification or modifications to the wild-type glycoprotein hormones described herein can be ascertained in any number of ways. For example, changes to second messenger systems within cells transfected with a nucleic acid encoding the modified glycoprotein hormones can be measured and compared to similar cells transfected with a nucleic acid encoding the wild-type glycoprotein hormone. Alternatively, the activity of a modified glycoprotein hormone can be determined from receptor binding assays, from thymidine uptake assays, from progesterone production assays, or from T4 secretion assays. One skilled in the art can readily determine any appropriate assay to employ to determine the activity of either a wild-type or a modified glycoprotein hormone.

In one embodiment of the present invention, the modified glycoprotein hormone has a potency which is increased over the potency of the wild type glycoprotein hormone. This increased potency can be assessed by any of the techniques mentioned above or in any other appropriate assay as readily determined by one skilled in the art. The increased potency does not have to be consistent from assay to assay, or from cell line to cell line, as these of course, will vary.

In another embodiment of the present invention, the modified glycoprotein hormone has a maximal efficacy which is increased over the maximal efficacy of the wild type glycoprotein hormone. This increased maximal efficacy can be assessed by any of the techniques mentioned above or in any other appropriate assay as readily determined by one skilled in the art. The increased maximal efficacy does not have to be consistent from assay to assay, or from cell line to cell line, as these of course, will vary.

Other assays suitable for characterizing the analogs described herein are described in PCT/US99/05908, which is herein incorporated by reference in its entirety. For instance, various immunoassays may be used including but not limited to competitive and non-competitive assay systems using techniques such as radioimmunoassays, ELISA, Isoelectric focusing (IEF) assays, sandwich immunoassays, immunoradiometric assays, gel diffusion precipitin reactions, immunodiffusion assays, in situ immunoassays, western blots, precipitation reactions, agglutination assays, complement fixation assays, immunofluorescence assays, protein A assays, and immunoelectrophoresis assays, etc.

For example, when the beta subunit is that of FSH, improvements in the quality and quantity of oocytes can be assessed by in vitro and in vivo assays. Superactive FSH can be used to improve the quality and quantity of oocytes from animals, including but not limited to, human, mouse, rat, primate, rabbit, pig, horse, sheep, and dog. Preferably, a superactive FSH is administered to a human or any animal. It is common for improvements in oocyte quantity and quality to be determined using different end points of the in vitro fertilization process such as oocyte formation, oocyte fertilization, and blastocyst formation. In vitro fertilization experiments may follow a "superovulation protocol" in which subjects are treated with a superactive FSH analog according to the present invention, which leads to the release and maturation of multiple oocytes. In in vitro fertilization experiments, FSH (superactive FSH and recombinant wild type FSH) may be administered with hCG to trigger ovulation. A control animal may be used which receives only hCG or pregnant mare serum gonadotropin (PMSG). The quality of oocytes can be improved by increasing the fertilization rate of oocytes in an animal. The fertilization rate of a superactive follicle stimulating hormone can be determined in vivo or in vitro by comparing the fertilization rate achieved with a superactive FSH to the fertilization rate achieved with the same amount of recombinant wild type FSH. A control animal may also be used that receives hCG. The rate of fertilization can be measured by the percent of two-cell embryos which develop per total number of oocytes. If fertilization takes place in vitro, two cell embryos can be counted in fertilization dishes. In mice, two cell embryos develop approximately twenty-four hours after fertilization. The fertilization rate varies based on the amount of superactive FSH administered. An animal may receive multiple does of superactive FSH. The rate of fertilization increases by at least about 10 percent as a result of administration of superactive FSH at the maximally effective dose for oocyte number. The rate of fertilization may increase by at least about 20 percent, preferably at least 30%, 40%, 50%, 60%, 70%, 80%, 90%, or 100% as a result of administration of superactive FSH at the maximally effective dose for oocyte number. Superactive follicle stimulating hormone can improve the quality of oocytes by improving the blastocyst formation rate per fertilized oocyte. The rate of blastocyst formation can be measured by determining the percentage of two-cell embryos which form blastocysts. The rate of blastocyst formation increases whether the blastocyst forms in vivo or in vitro. The blastocyst formation rate is dependent on the amount of superactive follicle stimulating hormone administered. The rate of blastocyst formation increases at least about 10 percent as a result of administration of a superactive follicle stimulating hormone at the maximally effective dose for oocyte number. The rate of blastocyst formation may increase at least about 20 percent, preferably at least 30%, 40%, 50%, 60%, 70%, 80%, 90%, or 100% as a result of administration of superactive FSH at the maximally effective dose for oocyte number.

Superactive follicle stimulating hormone can improve the quality of oocytes by increasing the total number of embryos per fertilized oocyte. The increase in total number of embryos per fertilized oocyte increases whether fertilization occurs in vivo or in vitro. The increase in total number of embryos per fertilized oocyte is dependent on the amount of superactive follicle stimulating hormone administered. The total number of embryos per fertilized oocyte increases at least about 10 percent as a result of administration of a superactive follicle stimulating hormone at the maximally effective dose for oocyte number. The total number of embryos per fertilized oocyte may increase by at least about 20 percent, preferably at least 30%, 40%, 50%, 60%, 70%, 80%, 90%, or 100% as a result of administration of superactive FSH at the maximally effective dose for oocyte number.

For example, when the beta subunit is that of CG, potent luteinizing hormone (LH)-like activities can be assessed by in vitro and in vivo bioassays. Superactive CG induces ovulation, extends the life span of corpus luteum, increases progesterone synthesis and promotes the formation of accessory corpora lutea in certain species. Such actions result in more effective oocyte collection, increase in oocyte quality in certain species, increase of pregnancy and pregnancy maintenance rates.

Glycoprotein Hormone Analogs with Increased Serum Half-Life

The modified glycoprotein hormone proteins of the invention may also be further modified such that the plasma half-life is increased as compared to wild type counterparts. The modified glycoprotein hormone proteins of the invention may further comprise a potential glycosylation site including sequences comprising N-glycosylation and/or O-glycosylation sites. For example, placement of the peptide NVTINV (SEQ ID NO: 1) or VNVTINVT (SEQ ID NO: 20) in the alpha subunit provides for potential glycosylation site of the alpha subunit. The peptides of SEQ ID NO: 20 or SEQ ID NO: 1 may be placed in the human wild type sequences between D3 and Q5. The peptides of SEQ ID NO: 20 or SEQ ID NO: 1 may be placed in the bovine, equine, porcine and ovine wild type sequences between F6 and T7. The inserted peptide may further comprise an additional threonine residue at the amino terminus. Further peptides to insert in order to alter glycosylation include NV, INV, and TNV peptides, as well as TNVTINV (SEQ ID NO: 12). For example, a modified alpha subunit of glycohormone may include an insert of NV between F6 and T7 plus an insert of INV between T7 and T8. Increased half-life may also be provided by pegylation or conjugation of other appropriate chemical groups or by constructing fusion proteins having increased half life or any other method. Such methods are known in the art, for instance as described in U.S. Pat. No. 5,612,034, U.S. Pat. No. 6,225,449, and U.S. Pat. No. 6,555,660, each of which is incorporated by reference in its entirety.

Half-life may also be increased by increasing the number of negatively charged residues within the molecule, for instance, the number of glutamate and/or aspartate residues. Such alteration may be accomplished by site directed mutagenesis. Such alteration may also be achieved via an insertion of an amino acid sequence containing one or more negatively charged residues into the modified glycoprotein hormone proteins.

The half-life of a protein is a measurement of protein stability and indicates the time necessary for a one-half reduction in the concentration of the protein. The serum half-life of the modified glycoprotein hormone proteins described herein may be determined by any method suitable for measuring hormone levels in samples from a subject over time, for example but not limited to, immunoassays using antibodies to measure levels in serum samples taken over a period of time after administration of the modified glycoprotein hormone proteins, or by detection of labeled hormone molecules, i.e., radiolabeled molecules, in samples taken from a subject after administration of the labeled glycoprotein hormones.

Methods of Treatment

The modified glycoprotein hormone proteins of the present invention may be used to treat any condition associated with glycoprotein hormone activity. The modified glycoprotein hormone proteins of the present invention may be used to treat a subject in need thereof. A subject may be an animal, such as a mammal, a reptile, a fish, a bird and an amphibiab. The subject may be a mammal, such as a human, cow, sheep, pig or horse. An animal includes livestock and domesticated pets, such as canines and felines. The subject may be a human patient or an animal in need of improved glycoprotein hormone activity. Conditions associated with glycoprotein hormone activity are ones that are either completely or partially caused by altered glycoprotein hormone responsiveness, or ones that benefit from the administration of glycoprotein hormone. For instance, such conditions include, but are not limited to ovulatory dysfunction, luteal phase defects, unexplained infertility, male factor infertility, time-limited conception, low FSH receptor expression, low FSH receptor sensitivity, FSH receptor binding deficiencies, FSH receptor coupling deficiencies, low testosterone production, male pattern baldness, and pituitary failure or injury.

For example, the quantity and quality of oocytes can be improved by administering a superactive FSH analog as described herein to an animal. For example, Applicants have surprisingly found that by administering a superactive FSH containing a modified alpha-subunit, a dramatic increase in the quantity and quality of oocytes is obtained. The effects of a superactive FSH on oocyte quantity and quality may be further enhanced by increasing the FSH serum half-life of the superactive FSH. The FSH serum half-life can be increased by further modifying the superactive FSH. Further modifications, including but not limited to those previously described, can be used to increase FSH serum half-life.

The modified FSH, CG, LH, or TSH glycoprotein hormone proteins of the present invention may also be used in therapeutic regimens of assisted reproduction in either a male or female subject comprising administering an assisting amount of the modified glycoprotein hormone proteins to the subject. In such methods, the analogs may be administered alone or in combination with other therapeutics, for instance, including but not limited to Clomiphene citrate and GnRH (gonotropin releasing hormone). The modified glycoprotein hormone proteins of the present invention may be administered as a combination of one or more glycoproteins. For example, a modified alpha subunit may be combined with a FSH beta subunit, a CG beta subunit, a TSH beta subunit, and/or a LH beta subunit, together or separately, and the modified glycoproteins are then administered to a subject. For example, in a subject with isolated gonadotropin deficiency (IGD), modified FSH, CG, TSH, and LH may be administered to the subject to restore normal gonadal function. It is widely known in the art that glycoprotein hormones such as FSH, CG, TSH, LH are integral in female reproductive physiology, and these glycoprotein hormones may be administered to a subject to overcome a number of reproductive disorders and thereby assist reproduction.

Single and multiple injection dosing regimens are tested for the modified equine CG glycoprotein. For superstimulation using eCG analog in horses, cows, or pigs, single or 2:1 split eCG analog injection is used. Dose ranging studies for eCG analog include a single im. injection of 30, 45, 60, 75, 90, 105 and 120 mcg. Optimized dose are tested in 2:1 ratio and the optional second split dose will coincide with PGF2alpha treatment on Day 6 or another date. The treatment with the modified eCG produces superovalation in horses, cows, and pigs.

A skilled practitioner in the art can readily determine the effective amount of the glycoprotein hormone to administer and will depend on factors such as weight, size, the severity of the specific condition, and the type of subject itself. The therapeutically effective amount can readily be determined by routine optimization procedures. The present invention provides glycoprotein hormones with increased potency relative to the wild-type glycoprotein hormone. These modified glycoprotein hormones will allow a skilled practitioner to administer a lower dose of a modified glycoprotein hormone relative to the wild-type glycoprotein hormones to achieve a similar therapeutic effect, or alternatively, administer a dose of the modified glycoprotein hormone similar to the dose of the wild-type glycoprotein hormone to achieve an increased therapeutic effect.

Depending on whether the glycoprotein hormone is administered orally, parenterally, or otherwise, the administration of the prostaglandin can be in the form of solid, semi-solid, or liquid dosage forms, such as, for example, tablets, pills, capsules, powders, liquids, creams, and suspensions, or the like, preferably in unit dosage form suitable for delivery of a precise dosage. The glycoprotein hormone may include an effective amount of the selected glycoprotein hormone in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected glycoprotein hormone without causing unacceptable biological effects or interacting in an unacceptable manner with the glycoprotein hormone. Actual methods of preparing such dosage forms are known, or will be apparent, to those skilled in this art; for example, see Remington's Pharmaceutical Sciences, latest edition (Mack Publishing).

The following examples are provided to describe and illustrate the present invention. As such, they should not be construed to limit the scope of the invention. Those in the art will well appreciate that many other embodiments also fall within the scope of the invention, as it is described hereinabove and in the claims.

EXAMPLES

Design of Alpha Subunit Analogs

A human FSH superagonist glycoprotein with modifications to the α-subunit at Q13R+E14R+P16R+Q20R (human 4R) with a wild-type β-subunit demonstrated significant binding superiority over their wild-type counterparts.

Table 1 shows a comparison of human alpha wild-type (WT) and selected hFSH superagonists primary amino acid structure. N-terminal portions of human alpha wild-type (amino acid residues 1-28 of 92 total residues) and mutated forms are shown. Location of 4 superagonist substitutions to arginine (R) is in the shaded area. Selected 4 different inserts introducing one or two additional N-linked carbohydrate chains are marked between amino acid D3 and Q5 of the wild-type sequence.

TABLE 1

| | |
|---|---|
| WT | APD V QDCPECTLQENPFFSQPGAPILQO |
| TR4401 (4R) | APD V QDCPECTLRRNRFFSRPGAPILQO |
| TR44701 (4R + Ins1) | APDVNVTINVTQDCPECTLRRNRFFSRPGAPILQO |
| TR44601 (4R + Ins2) | APD NVTINVTQDCPECTLRRNRFFSRPGAPILQO |
| TR44201 (4R + Ins3) | APD NVTQDCPECTLRRNRFFSRPGAPILQO |
| TR44301 (4R + Ins4) | APDV NVTQDCPECTLRRNRFFSRPGAPILQO |

The segments in Table 1 are listed as the following: SEQ ID NO: 43: hFSH WT; SEQ ID NO: 33, hFSH alpha (4R); SEQ ID NO: 34, hFSH alpha (4R+Ins1); SEQ ID NO: 35, hFSH alpha (4R+Ins2); SEQ ID NO: 36, hFSH alpha (4R+Ins3); SEQ ID NO: 37, hFSH alpha (4R+Ins4).

The bovine FSH (bFSH) substitutions in some embodiments are highly analogous to the residues previously mutagenized in the human FSH alpha subunit and include combination of 5 mutations called "5R" (K15R+K17R+E18R+K20R+K24R). E.g. SEQ ID NO: 7. To increase the probability that introduced glycosylation recognition sequences (NXT or NXS) leads to attachment of N-linked carbohydrate chain, 18 different bovine alpha subunit constructs were established and cloned into previously developed expression vectors. 12 constructs contained N-terminal extension peptide sequences ANITV, ANTTA, ANTSA, ANITVNITV, ANTSANTTA and ANTSANTSA.

Table 2 shows a comprison of bovine alpha wild-type (WT) and selected bFSH superagonists primary amino acid structures. N-terminal portions of bovine alpha wild-type (amino acid residues 1-32 of 96 total residues) and mutant bovine alpha are shown. Location of 5 superagonist substitutions to arginine (R) or lysine (K) are marked in the shaded area between amino acids C14 and P25, coded as 5R of 4R+1K. Selected 4 different inserts introducing one or two additional N-linked carbohydrate chains are marked in between amino acid F6 and T8 of the wild-type sequence.

The segments in Table 2 are listed as the following: SEQ ID NO: 44, WT bFSH; SEQ ID NO: 23, bFSH alpha (5R); SEQ ID NO: 24, bFSH alpha (4R+1K); SEQ ID NO: 25, bFSH alpha (5R+Ins1); SEQ ID NO: 26, bFSH alpha (5R+Ins2); SEQ ID NO: 27, bFSH alpha (5R+Ins3); SEQ ID NO: 28, bFSH alpha (5R+Ins4); SEQ ID NO: 29, bFSH alpha (4R+1K+Ins1); SEQ ID NO: 30, bFSH alpha (4R+1K+Ins2); SEQ ID NO: 31, bFSH alpha (4R+1K+Ins3); SEQ ID NO: 32, bFSH alpha (4R+1K+Ins4).

TABLE 2

| | | | | | |
|---|---|---|---|---|---|
| WT | FPDGEF | | TMQGCPEC | KLKENKYFSK | PDAPIYQC |
| 5R | FPDGEF | | TMQGCPEC | RLRRNRYFSR | PDAPIYQC |
| 4R + 1K | FPDGEF | | TMQGCPEC | RLRRNRYFSR | PDAPIYQC |
| 5R + Ins1 | FPDGEF | NVTINV | TMQGCPEC | RLRRNRYFSR | PDAPIYQC |
| 5R + Ins2 | FPDGEF | TNVTINV | TMQGCPEC | RLRRNRYFSR | PDAPIYQC |
| 5R + Ins3 | FPDGEF | NV | TMQGCPEC | RLRRNRYFSR | PDAPIYQC |
| 5R + Ins4 | FPDGEF | TNV | TMQGCPEC | RLRRNRYFSR | PDAPIYQC |
| 4R + 1K + Ins1 | FPDGEF | NVTINV | TMQGCPEC | RLRKNRYFSR | PDAPIYQC |
| 4R + 1K + Ins2 | FPDGEF | TNVTINV | TMQGCPEC | RLRKNRYFSR | PDAPIYQC |
| 4R + 1K + Ins3 | FPDGEF | NV | TMQGCPEC | RLRKNRYFSR | PDAPIYQC |
| 4R + 1K + Ins4 | FPDGEF | TNV | TMQGCPEC | RLRKNRYFSR | PDAPIYQC |

Equine glycoprotein alpha subunits including mutations were also produced and some embodiments include substitution of K15R, E18R, K2OR, and K24R. E.g. SEQ ID NO: 9; SEQ ID NO: 38-40. In addition, equine glycoprotein alpha subunits having K15R, E18H, K20R, and K24R were also generated (e.g. SEQ ID NO: 41; SEQ ID NO: 42). These mutated alpha subunit also contain insert of NVTINV (SEQ ID NO: 1) between F6 and T7 of the subunit (e.g. SEQ ID NO: 9, 40, and 42) or NV insert between F6 and T7 plus INV between T7 and T8 (e.g. SEQ ID NO: 38, 39, and 41).

Transient transfection of bFSH analogs using polyethylenimine (PEI) resulted in 3.7-4.5 fold increase in bFSH analog expression in comparison to lipofectamine-based methods (data not shown). Expression levels of various FSH analogs based on heterodimer-specific ELISA indicated no major loss of FSH dimer formation and do not support previous claims that a single chain construct was necessary to achieve high level expression.

Figure 2:
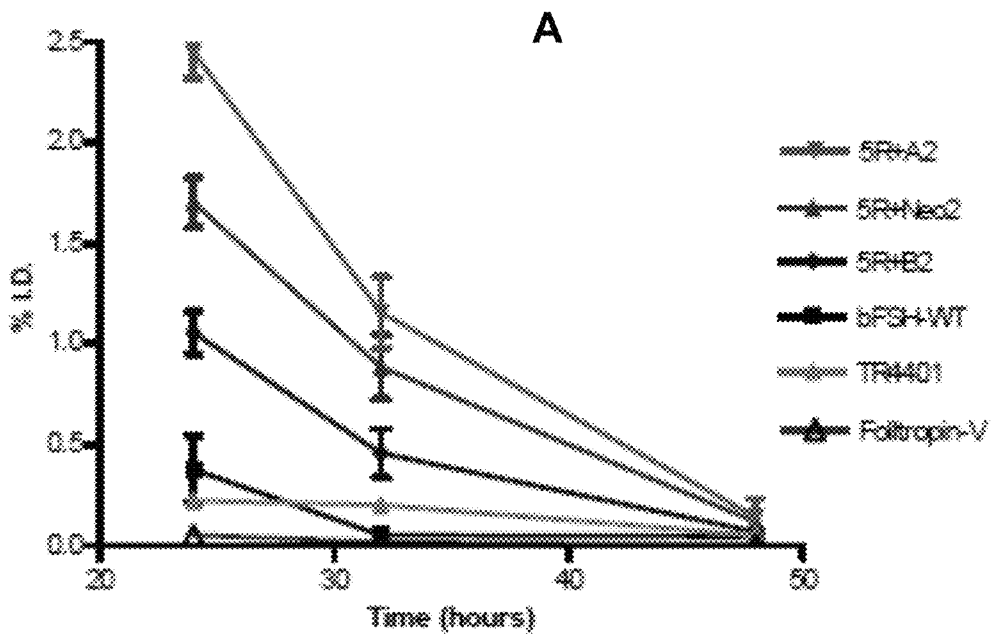
FIGS. 2A and 2B show PK screening assay of various bFSH analogs after single subcutaneous injection in mice. In each experiment, 5 mice were used for each preparation. Blood samples were taken at 24, 32 and 48 h after injection, plasma levels were deducted and the data were expressed as % of injected dose (% ID). FSH levels in plasma samples were assayed using FSH ELISA (Endodrine Technologies).
Figure 2:
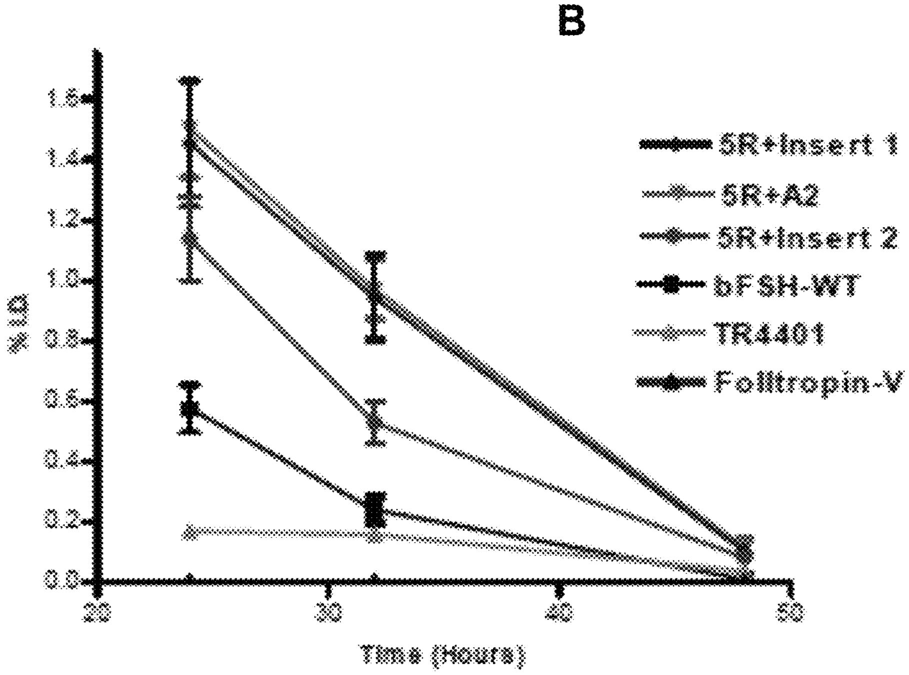
Figure 3:
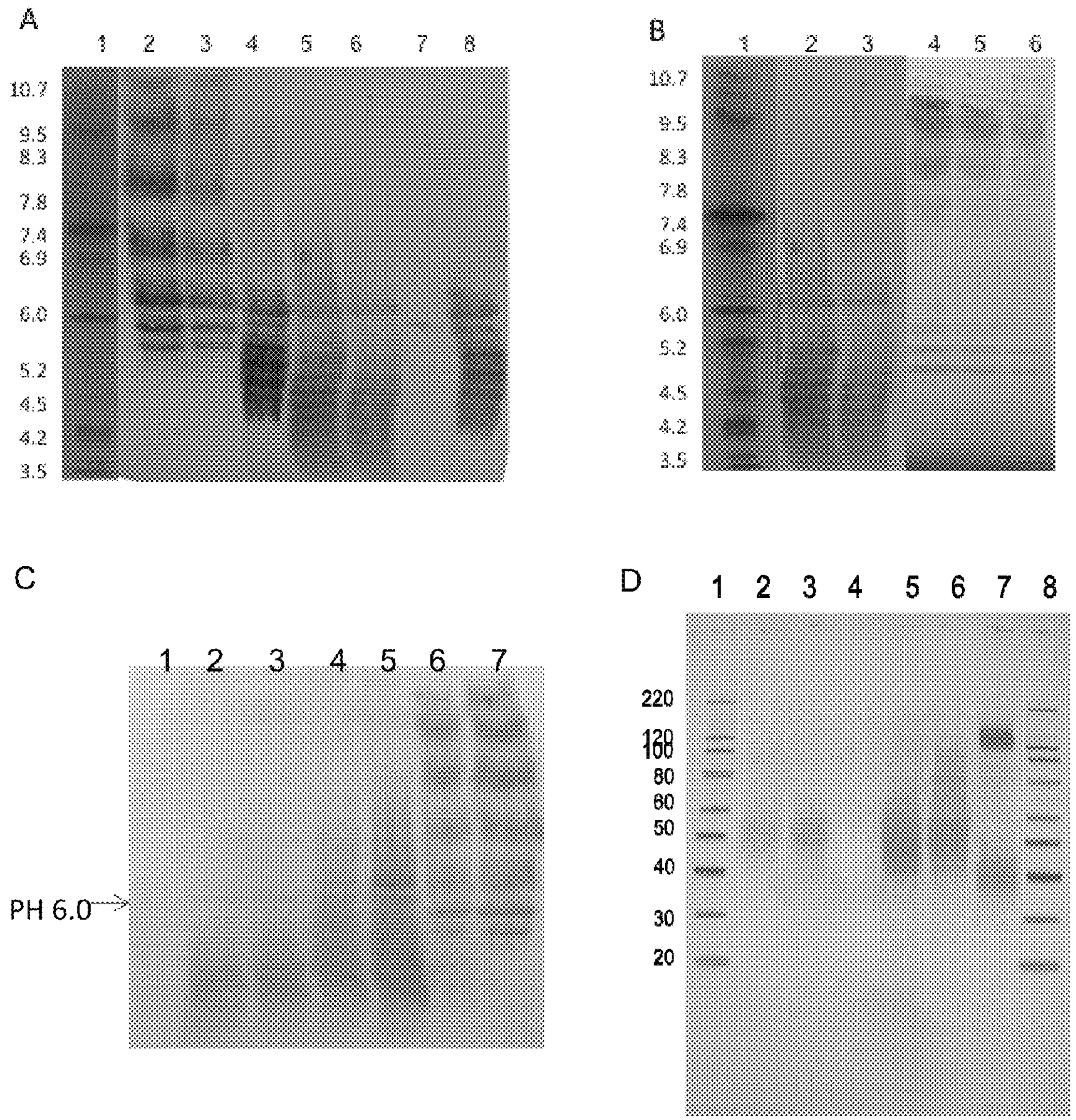
FIGS. 3A-D show the analysis of different lots of TR55601 production.

Selection of transiently expressed bFSH analogs included cAMP-based in vitro bioassay and PK screening assays (see FIGS. 1 and 2). There was a significant 3-4 fold increase in potency of bFSH with 5R substitutions in comparison to porcine FSH (pFSH-Folltropin®-V) and bFSH controls (FIG. 1A). Remarkably, in contrast to many previous studies (FIG. 1B), (Heikopp, Eur. J. Biochem 261: 81-84, 1999; Trousdale, Fertil. Steril. 91: 265-270, 2009) novel neoglycosylation inserts have been found not to decrease in vitro bioactivity of bovine FSH 5R analog (FIG. 1C). Identical neoglycosylation sites added at the N-terminus reduced in vitro bioactivity of bFSH, similar to the attenuating effect of neoglycosylation on the intrinsic activity of erythropoietin (Elliott, Exp. Hematol. 32: 1146-1155, 2004; Elliott, Nat. Biotechnol. 21: 4144-421, 2003; Sinclair, J. Pharm. Sci. 94: 1626-1635, 2005) and the effect of many other prolongations of half-life approaches including site-directed pegylation (Fishburn, J. Pharm. Sci. 97: 4167-4183, 2008; Uchiyama, Vet. J. 184: 208-211, 2010). Two days PK screening study in mice indicated that all neo-glycosylated bovine FSH "5R" analogs had increased terminal half life in comparison to bFSH-WT and Folltropin®-V (FIGS. 2A and 2B). The data from the PK screening assay indicated greatly prolonged plasma half-life due to glycosylation at one or two introduced neoglycosylation sites (Insert 1 and 2) in comparison to bFSH-WT, Folltropin®-V and TR4401 controls. Observed levels were comparable with bFSH-single chain molecule with 29 amino acid linker and 4-5 O-linked carbohydrate chains. Two initially tested analogs made as a combined superagonist and neoglycosylation inserts, named "Insert 1 and 2" had in vitro bioactivity comparable to 5R superagonist control alone (FIG. 1C) and yet still prolonged half life in mice (FIG. 2B). Such long acting analogs without reduction of superagonist activity are unprecedented and translates to expected impressive performance in vivo in cows.

Several hundreds of milligrams of various human FSH and TSH were produced recombinantly (rFSH or rTSH) with CHO cells using flasks, shakers, roller bottles and bioreactors. During initial work a dicistronic retroviral vector system was optimized for high level expression of FSH and TSH analogs in CHO-DG44 cells. Human rFSH preparation was tested. A single 60 μg dose of rFSH induced follicle development resulting in high number of good quality embryos matching previously optimized eight injections of Folltropin®-V (300 mg) administered twice daily over 4 days further supporting its unique properties such as delayed absorption after I.M. injection, as well as enhanced FSH receptor residency time. See FIGS. 3 and 5-8. The rFSH superagonist at a 10 μg dose showed exceptional ability to recruit and maintain over 12 days enhanced pool of growing follicles, in particular follicles in 3-5 mm size range, which are also known in humans to have low FSH receptor number (data not shown). This unexpected enhancement and support of small follicles by the rFSH, not observed with previously optimized dosing of control Folltropin®-V, provides a new way to recruit FSH responsive follicles at random stages of the cycle and enhance potential for successful IVF and superovulation in a number of poor responders caused by decreased FSH receptor number or function (Perez Mayorga, J. Clin. Endocrinology 152: 3268-3369, 2000; Levallet, Arch. Med. Red. 30: 486-494, 1999; Rannikko, Mol. Hum. Reprod. 8: 311-317, 2002; Cai, Feril. Steril. 87: 1350-1356, 2007). However, because of the 40 amino acid difference between bovine FSH and human FSH based-alpha subunit with 4 arginine substitutions there were observed some carryover effects from previous treatments with the rFSH in the same cows, which was in agreement with previous data study showing immunogenic properties of human FSH in rabbits and Rhesus monkeys (Cai, Int. J. Toxicol. 30: 153-161, 2011; De Castro, Theriogenology 72: 655-662, 2009).

The introduction of arginine (R) or lysine (K) residues into a selected modification permissive area of the common alpha-subunit has been previously shown to modulate activity of glycoprotein hormones during evolution (Szkudlinski, Nat. Biotechnol. 14: 1257-1263, 1996; Szkudlinski, Physiol. Rev. 82: 473-502, 2002) and play an important role in the electrostatic interaction with the negatively charged cluster located in the hinge region of glycoprotein hormone receptors (Mueller, Trends Endocrinol. Metab. 21: 111-122, 2010; Mueller, J. Biol. Chem. 284: 16317-16324, 2009; Mueller, Endocrinol. 152: 3268-3278, 2011). Specific bFSH superagonist development includes minimal substitutions to 4-5 R and/or K to produce a more potent and efficacious molecule with possible delayed absorption to increase duration of action as shown in the data herein and other studies for hFSH and other glycoprotein hormone analogs (Szkudlinski, Physiol. Rev. 82: 473-502, 2002). The minimal length amino acid inserts containing one or two carbohydrate neoglycosylation sites to increase halflife to produce a single injection analog without reducing increased superagonist potency/efficacy has also been investigated (see FIG. 4). For further analysis, 8 constructs containing peptide inserts NVTINV, NVTINVT, NV and NVT located between amino acid 6 and 8 of the wild-type sequence can be used. As shown in the data herein and in contrast to previous neoglycosylation and pegylation studies (Trousdale, Feril. Steril. 91: 265-270, 2009; Uchiyama, Vet J. 184: 208-211, 2010; Perlman, J. Clin. Endocrinol. Metab. 88: 3227-3235, 2003) it is possible to engineer minimal length amino acid insert containing complex carbohydrate to increase half-life without reducing increased superagonist potency/efficacy. These novel analogs can be expressed by transient transfection in CHO-K1 cells using the optimized high expression system method using PEI and roller bottles.

Purification of selected 4-6 analogs expressed by transient transfection may be performed using a capture step using SP Sepharose column, followed by selecting analogs with Mono Q ion exchange chromatography before final polishing using gel filtration. The purity of bFSH analogs can be greater than 98%. Cumulative recovery may reach 50% with a total 50-fold purification. All analogs may be characterized in vitro by ELISA immunoassay, robust in vitro cAMP bioassay using CHO-FSHR cell line, SDS-PAGE electrophoresis and isoelectric focusing (IEF) gel analysis. Selected purified analogs may also be analyzed by rigorous quantification by reverse phase HPLC, carbohydrate compositional analysis and assessments of stability and aggregation states.

Further experiments produced bovine FSH analog TR55601 (alpha subunit: SEQ ID NO: 7), which includes substitutions to arginine (R) in 15K, 17K, 18K, 20K, and 24K of the alpha subunit as well as an NVTINV (SEQ ID NO: 1) insert between 6F and 7T of the alpha subunit. Several lots of TR55601 were generated and tested using IEF and Western blot analysis. FIGS. 3A-D show exemplary results of the analysis. FIGS. 3A-3D demonstrate, in part, that TR55601/Lot 4 and Lot 5 display optimal distribution and verify the effectiveness of the mutations in this Lot. Lots 4 and 5 and Lots having similar screening results were used in animal treatments. For example, the IEF-Western Blot analysis illustrate the optimized acidic isoforms of TR56001 of Lot 4 and Lot 5 in FIGS. 3A-C. On the other hand, as shown in FIGS. 3A and 3C, Lot 3 was not fully verified and was not used in animal treatments. The bFSH analogs and in particular the samples of TR55601 were also studied with PK screening assays in mice. Mice were subcutaneously injected with selected bFSH samples and blood samples were taken at 24, 32, and 48 hours after injections. Plasmas were isolated and analyzed with bFSH ELISA (Endocrine Technologies, Inc.). The prolonged half life of Lot 4 of the TR55601 samples was confirmed with the PK screening assays. Data not shown.

Full pharmacokinetic profile of selected candidate analogs may be performed in by sc administration of a single dose of 10 μg per rat and 10 different blood collections times (1, 5, 15, 30 min and 1, 2, 6, 24 and 48 h) spanning both distribution and elimination phase. Bovine FSH plasma levels may be quantified in plasma using bFSH-ELISA. Full PK analysis may be performed.

Analogs were selected for constructing bicistronic expression vectors, and selection and amplification of analog expression in CHO-DG44 cells in preparation for large-scale production, purification and superovulation studies in cattle. The CHO-DHFR(−) DG44 cells were co-transfected with the expression vectors and submitted to gene amplification in culture medium containing stepwise increments of methotrexate (MTX). Cells were qualified for the next amplification step after regaining their polygonal morphology (2-3 weeks). Clones that present a secretion level>2 pg/cell/day may be subjected to a second treatment, directed to amplify the GS marker gene (MSX). An additional 2-5 fold increase may be obtained, reaching a secretion level up to 10 pg/cell/day.

Preparation and Experimentation with Alpha Subunit Analogs

Although the rFSH induced a superovulatory response following a single intramuscular (I.M.) injection and 60 μg would appear to be very close to the optimal dose, there was a significant decrease in superovulatory response when cows were exposed to the rFSH for three times or more. Therefore, experiments were designed to test a new rFSH formulation called TR 55601 rFSH, which includes an alpha subunit (SEQ ID NO: 7) having a “5R” substitution and an insert of NVTINV (SEQ ID NO: 1) between F6 and T7. The objective was to first determine the effect of a single or split dose treatment with rFSH to induce a superovulatory response in beef cows and then to further evaluate the superovulatory response of the single injection of rFSH and to determine if the superovulatory response remained high when cows were exposed to rFSH two or three times.

The TR55601 FSH samples were analyzed in vivo in rats with the classic Steelman-Pohley FSH bioassay (Steelman et al., Endocrinol. 53: 604-616, 1953). Female Sprague-Dawley rats (200-220 g) were injected with one single dose of test article (e.g. bFSH) or vehicle, supplemented with 40 IU of hCG. Ovarian weights were measured 72 hours after dosing. See FIG. 4. Each group is treated with hCG to provide a baseline. TR55601 bFSH, at all concentrations, significantly increases ovarian weight.

Figure 5:
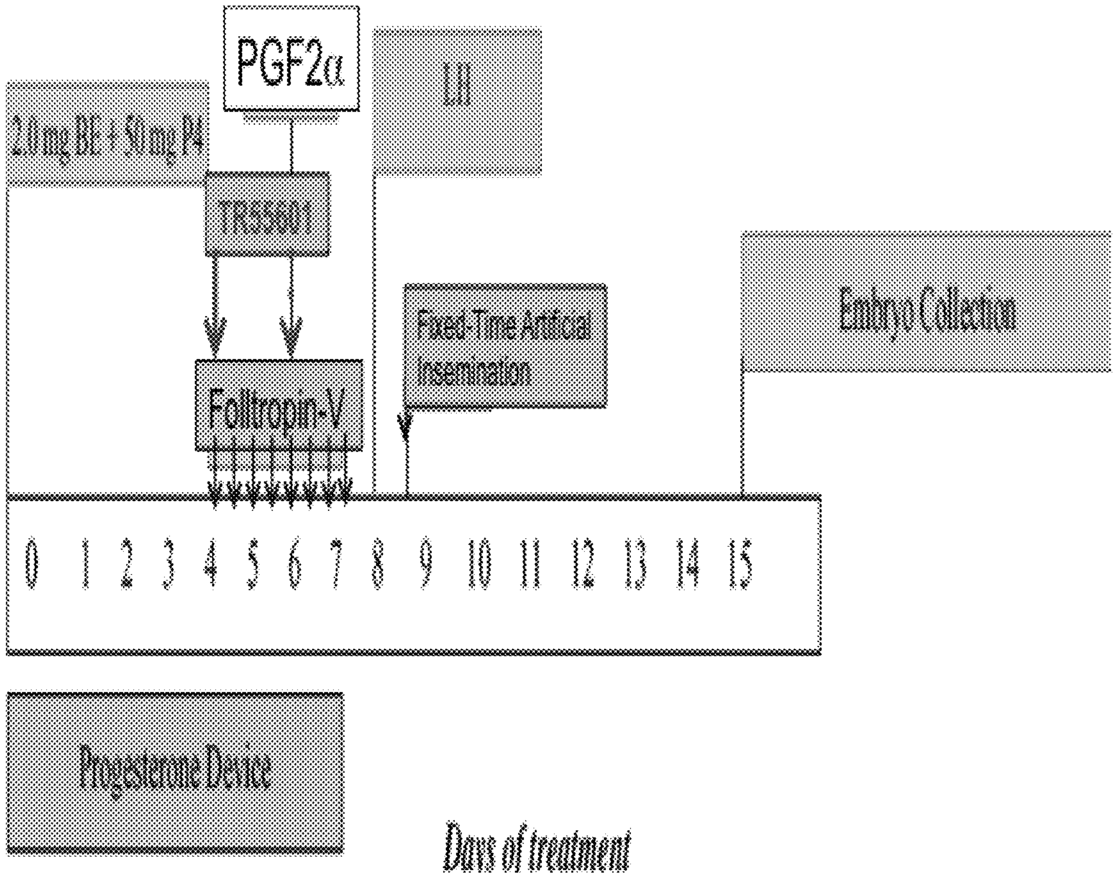
FIG. 5 demonstrates a follicular wave synchronizing protocol for superovulation, induction of ovulation and fixed-time artificial insemination. The 8 injections of Folltropin-VR (Bioniche) are replaced with a single or double injection of TR55601.

FIG. 5 shows a follicular wave synchronizing protocol for superovulation, induction of ovulation and fixed-time artificial insemination, wherein the 8 injections of Folltropin-VR (Bioniche) are replaced with a single or double injection of TR55601. Treatment included insertion of progesterone (P4) releasing intravaginal device and administration of benzoate estradiol (BE) on Day 0. Superovulatory treatments were initiated on Day 4 with TR55601 given as a single or double injection. Second split-dose injection was coinciding with $PGF_{2\alpha}$ treatments on Day 6. Progesterone device was removed with the last FSH injection on Day 7. On day 8 donors were receiving porcine LH and were inseminated without estrus detection 12 and 24 h later, or once on Day 8 (16 h after pLH). Ova/embryos were collected non-surgically on Day 15 (2, 3). Folltropin-V® was used as a control; total 300 mg* was given in 8 intramuscular (IM) injections twice daily over 4 days (mg*—based on highly impure NIH-FSH-P1 Reference Standard).

In particular, 30 nonlactating Red Angus cows were stratified and blocked based on their previous history of embryo production and randomly assigned to one of three treatment groups. Cows in the Control group (n=10) received 300 mg Folltropin-V, I.M. in a twice daily decreasing dose protocol administered over a 4-day period. Specifically: Day 4, 3.0 mL (am and pm); Day 5, 2.5 mL (am and pm); Day 6, 1.5 mL (am and pm) and Day 7, 0.5 mL (am and pm). Cows in the rFSH 60 μg treatment group received a single I.M. injection of 60 μg rFSH and cows in the rFSH 40-20 μg treatment group received an I.M. injection of 40 μg rFSH on Day 4, followed by another I.M. injection of 20 μg rFSH on Day 6.

Then, 25 out of the 30 cows were superstimulated again with Folltropin-V (Control) or a single injection of 60 μg of rFSH Animals in the Control group (n=10) remained in the Control group, and 8 out 10 cows in the rFSH 60 μg in Experiment 1 were treated again by a single I.M. injection of rFSH. Furthermore, 7 out of 10 cows previously treated with the split-single injection of rFSH were treated with a single I.M. injection of rFSH. The interval between the embryo collections was 29 days.

In each experiment, data points were first evaluated for normality and homogeneity of variance. Because variances differed among groups, data were transformed by square root and analyzed by one-way ANOVA. Analysis of the overall response after the three experiments are concluded will be done by two-way ANOVA to detect the effect of experiment number and treatment and their interaction. Means were compared by the protected LSD test. Follicle data were analyzed by the MIXED procedure to detect the effect of treatment, day and their interaction on follicle numbers and growth profiles. All analyses were done using the Infostat Analytical Software (Universidad Nacional de Cordoba, Argentina).

Superovulatory response and ova/embryo data are summarized in Table 3. Although the mean number of CL and cows with ≤2 CL on the day of ova/embryo collection did not differ among groups, the split-injection of rFSH resulted in a higher ($P<0.05$) number of unovulated follicles. The mean number of total ova/embryos, fertilized ova and transferable embryos (Grades 1, 2 & 3) also did not differ.

Table 3 shows superovulation with single or split-single doses of TR55601 (rFSH).

TABLE 3

Mean (±SEM) number of corpora lutea (CL), follicles >10 mm in diameter, number of cows with ≤2 CL at the time of ova/embryo collection, number of ova/embryos, fertilized ova and grades 1, 2, and 3 embryos (transferable embryos) in beef cows treated with a single (60 μg) or split-single (40-20 μg) I.M. injections of rFSH (TR55601) or 300 mg Folltropin-V ® (Control) given in twice daily IM injections over 4 days.

| Treatment | N | CL | Follicle >10 mm | Cows with ≤2 CL on Day 15 | Total ova/embryos | Fertilized ova | Grade 1 embryos | Grades 1&2 embryos | Grades 1, 2, &3 embryos | No. “0” emb |
|---|---|---|---|---|---|---|---|---|---|---|
| Control | 10 | 14.1 ± 2.1 | 3.2 ± 1.1a | 0 | 12.7 ± 2.4 | 10.5 ± 1.6 | 7.5 ± 1.4 | 8.1 ± 1.4 | 9.0 ± 1.5 | 0 |
| rFSH 60 μg | 10 | 12.7 ± 2.8 | 4.6 ± 1.1ab | 2 | 11.6 ± 3.0 | 9.1 ± 2.2 | 5.4 ± 1.2 | 6.6 ± 1.5 | 6.6 ± 1.5 | 2 |
| rFSH 40-20 μg | 10 | 13.9 ± 1.5 | 8.5 ± 1.9b | 0 | 11.2 ± 1.9 | 9.9 ± 1.8 | 6.2 ± 1.4 | 7.4 ± 1.7 | 7.9 ± 1.7 | 0 |
| P-value | | 0.6407 | 0.0262 | 0.1173 | 0.7317 | 0.6008 | 0.4339 | 0.6035 | 0.4462 | 0.1173 |

24 of the 25 cows used in the second experiment were superstimulated again with Folltropin-V (Control) or a single injection of 60 μg of rFSH. Again, Control cows remained in the Control group and rFSH cows remained in the rFSH group. The interval between embryo collections is 30 days.

On Day 0 (beginning of experiment), all animals received 5 mg estradiol-1713 plus 50 mg progesterone and an intravaginal device impregnated with progesterone (Cue-Mate, Bioniche Animal Health). On Day 4 (expected day of follicle wave emergence), all cows were superstimulated according to the groups described above. The 60 μg doses for the single I.M. injection rFSH constituted 7.5 mL and Folltropin-V was administered in 8 I.M. injections in a decreasing dose protocol. All animals received 500 μg of cloprostenol I.M. (Cyclase, Syntex, Argentina) on Day 6 in the morning and in the evening. Cue-mates were removed in the evening of Day 6. In the morning of Day 8, cows received 100 μg of gonadorelin (Gonasyn, Syntex Argentina) and inseminated 12 and 24 hours later. All cows were inseminated with frozen semen from the same bull. Ova/embryos were collected non-surgically on Day 15 and evaluated following IETS recommendations.

All cows were examined ultrasonically on Days 0, 4, 6 and 8 for the presence of a CL and follicle size and number and to determine follicle growth profiles. Ovulatory response was confirmed by counting the number of CL and follicles >10 mm in diameter by ultrasonography and rectal palpation on Day 15.

The superovulatory response and ova/embryo data for the second dosing are summarized in Tables 4 and 5. The mean number of CL, follicles >10 mm and cows with <2 CL on the day of ova/embryo collection did not differ between groups. The mean number of total ova/embryos, fertilized ova and transferable embryos (Grades 1, 2 and 3) also did not differ between groups.

Tables 4 and 5 show superovulation with single dose of TR55601 (rFSH).

TABLE 4

Mean (±SEM) number of CL, follicles > 10 mm in diameter and number of cows with ≤2 CL at the time of ova/embryo collection. Cows were treated with a single (60 μg) I.M. injection of rFSH or 300 mg Folltropin-V (Control) given in twice daily I.M. injections over 4 d.

| Treatment | N | CL | Follicles > 10 mm | Cows with ≤2 CL on Day 15 |
|---|---|---|---|---|
| Control | 10 | 12.7 ± 2.4 | 3.7 ± 0.9 | 0 |
| rFSH 60 μg | 15 | 14.7 ± 1.9 | 5.3 ± 1.3 | 1 |
| P-value | | 0.5730 | 0.3752 | 0.4047 |

TABLE 5

Mean (± SEM) number of ova/embryos, fertilized ova and grades 1, 2, and 3 embryos (transferable embryos) in beef cows treated with a single (60 μg) I.M. injection of rFSH (TR55601) or 300 mg Folltropin-V ® (Control) given in twice daily IM injections over 4 days.

| Treatment | N | Total ova/ embryos | Fertilized ova | Grade 1 embryos | Grades 1 & 2 embryos | Grades 1, 2 &3 embryos (transferable) | Cows with "0" transf. emb. |
|---|---|---|---|---|---|---|---|
| Control | 10 | 11.9 ± 2.5 | 10.5 ± 2.2 | 3.2 ± 0.8 | 4.7 ± 1.1 | 4.9 ± 1.2 | 2 |
| rFSH 60 μg | 14 | 13.4 ± 3.3 | 11.6 ± 3.0 | 3.5 ± 1.0 | 5.1 ± 1.5 | 6.1 ± 1.8 | 4 |
| P-value | | 0.8263 | 0.7958 | 0.8903 | 0.8608 | 0.9992 | 0.6326 |

For the final dosing experiment, only follicle data are available at this time. There was no significant difference in follicle growth profiles and the numbers of follicles on the day before insemination between the rFSH and Folltropin-V groups. Ovulation and ova/embryo data will be available shortly and will be presented separately for Experiment 3 and then combined with Experiments 1 and 2. Follicle data for Experiment 3 are available and have been combined with that of experiments 1 and 2 and are presented in Table 6.

Table 6 shows three superovulations with TR55601 (rFSH) at 30 day intervals.

Figure 6:
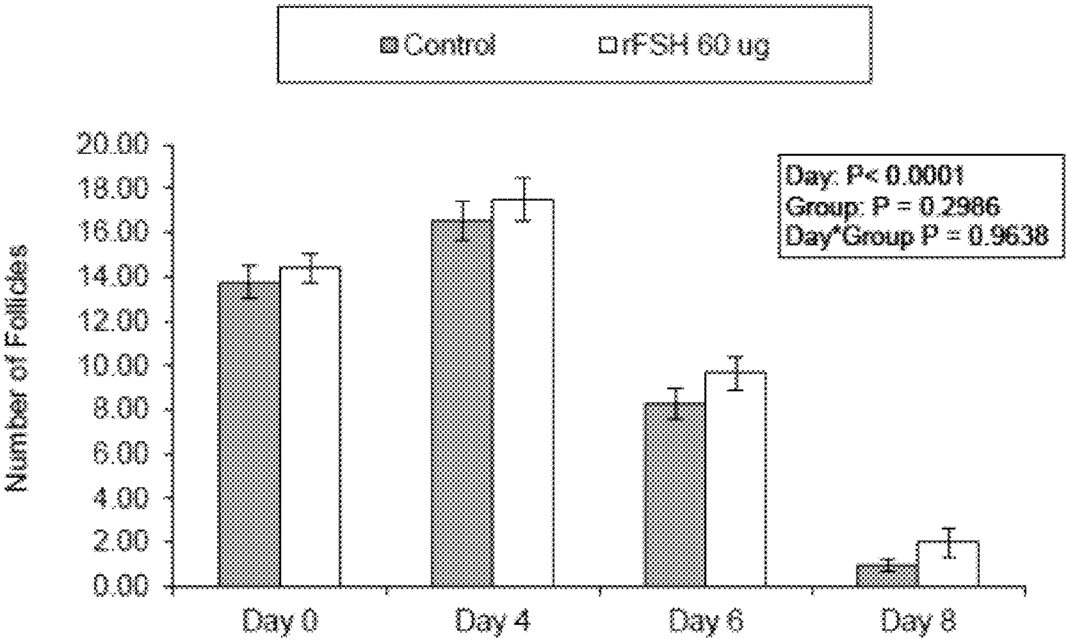
FIG. 6 shows the mean number of follicles (3 to 5 mm in diameter) during superstimulation treatment in beef cows treated with 60 μg rFSH given by a single I.M. injection or 300 mg Folltropin-V (Control) given in twice daily I.M. injections over 4 days (3 experiments combined).
Figure 7:
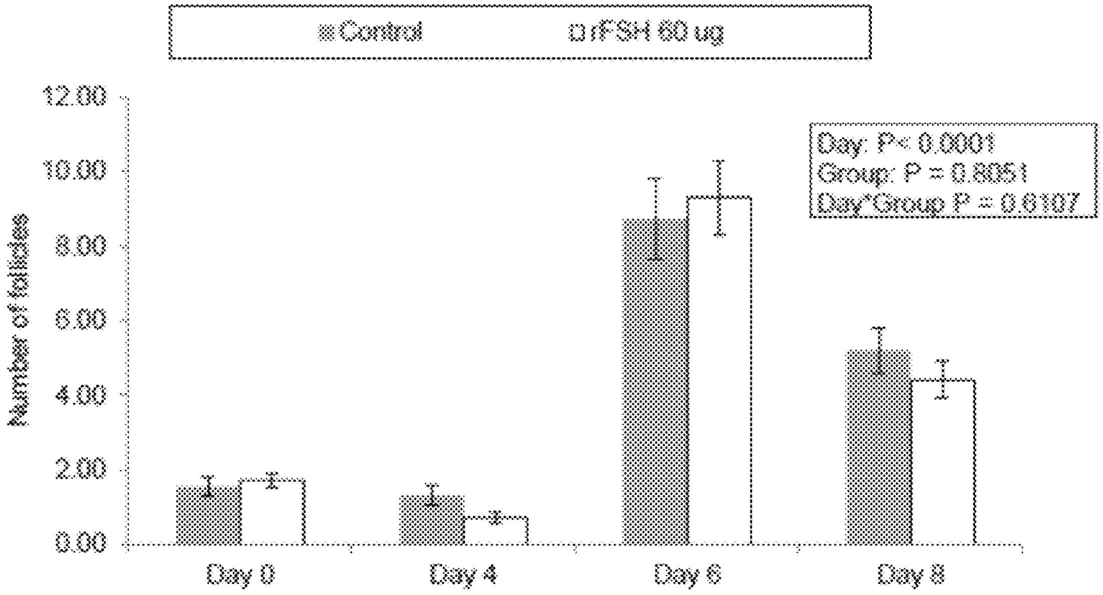
FIG. 7 shows the mean number of follicles 6 to 8 mm in diameter during superstimulation treatment in beef cows treated with 60 μg rFSH given by a single I.M. injection or 300 mg Folltropin-V (Control) given in twice daily I.M. injections over 4 days (3 experiments combined).
Figure 8:
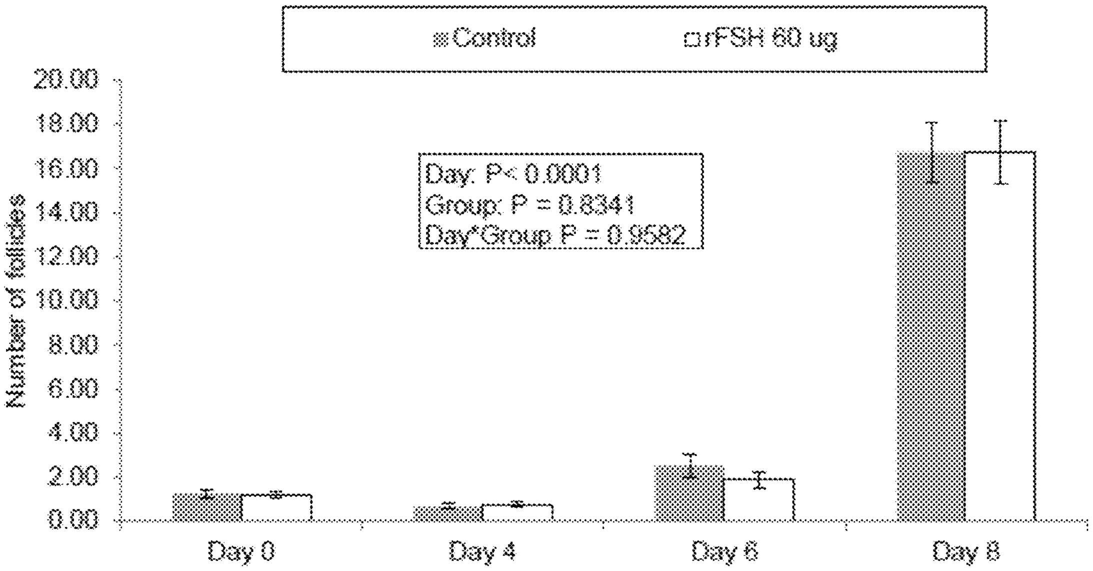
FIG. 8 shows the mean number of follicles >9 mm in diameter during superstimulation treatment in beef cows treated with 60 μg rFSH given by a single I.M. injection or 300 mg Folltropin-V (Control) given in twice daily I.M. injections over 4 days (3 experiments combined).
Figure 9:
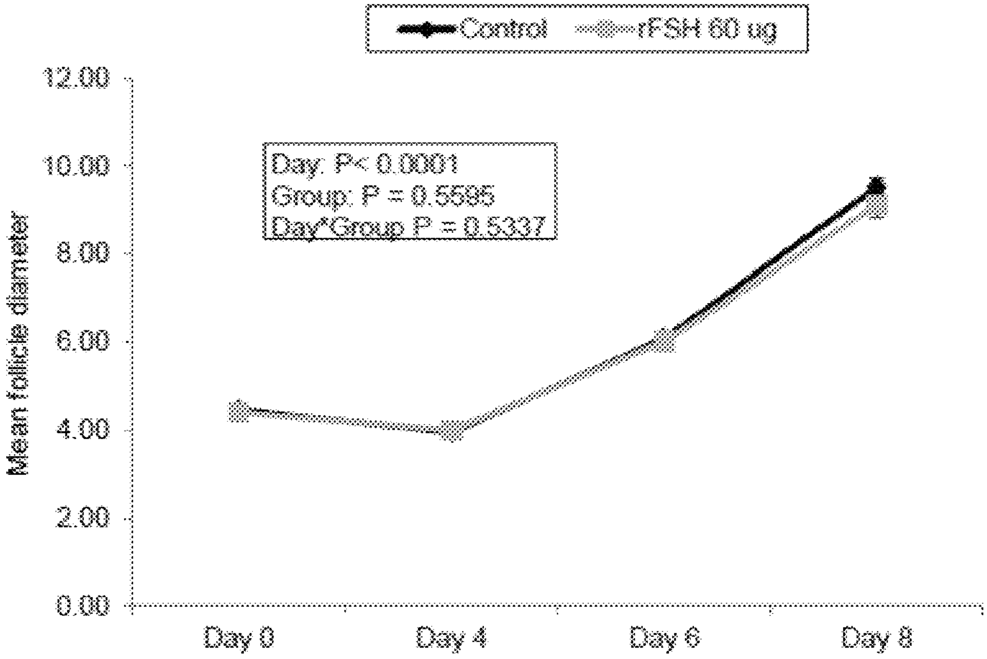
FIG. 9 shows the mean diameter profiles of all follicles ≥3 mm in diameter during superstimulation treatment in beef cows treated with 60 μg rFSH given by a single I.M. injection or 300 mg Folltropin-V (Control) given in twice daily I.M. injections over 4 days (3 experiments combined).
Figure 10:
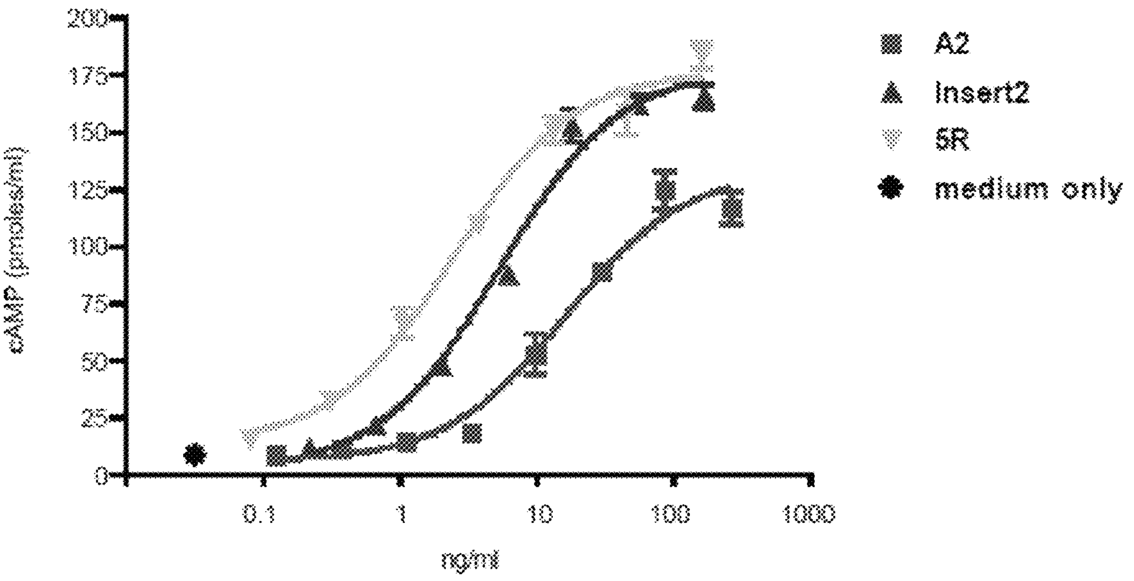
FIG. 10A shows a comparison in cAMP production for the insert in the human alpha subunit (A2), the insert without the amino-terminal valine (Insert 2), the 5 arginine substitutions only without the insert (5R) and control of medium only.
FIG. 10B shows the EC50 for the three constructs tested.

The numbers of follicles 3 to 5 mm in diameter did not differ among treatment groups (FIG. 6). Neither did the numbers of follicles 6 to 8 mm in diameter (FIG. 7), follicles >9 mm (FIG. 8) or the mean follicle diameter over the days of treatment differ (FIG. 9).

Results obtained in this series of experiments can be interpreted to suggest that the rFSH product induces a superovulatory response in beef cows that is not different from that of Folltropin-V. There is also no evidence of a decrease in superovulatory response as compared with Folltropin-V when cows are treated three times consecutively. The supero-

TABLE 6

Mean (±SEM) number of CL, follicles >10 mm in diameter, number of cows with ≤2 CL at the time of ova/embryo collection, number of ova/embryos, fertilized ova and grades 1, 2, and 3 embryos (transferable embryos) in beef cows treated with a single (60 μg) or split-single (40-20 μg) I.M. injections of rFSH (TR55601) or 300 mg Folltropin-V ® (Control) given twice daily IM injections over 4 days. Cows were treated three consecutive times at ~30 day intervals (3 experiments combined).

| Experiments | N | CL | Follicles >10 mm | Cows with ≤2 CL on Day 15 | Total ova/embryos | Fertilized ova | Grade 1 embryos | Grades 1 & 2 embryos | Grades 1, 2 & 3 embryos (transferable) | Cows with "0" transt. emb |
|---|---|---|---|---|---|---|---|---|---|---|
| Main Effects | | | | | | | | | | |
| Experiment 1 | 24 | 14.1 ± 1.4 | 5.0 ± 1.0 | 1 | 13.0 ± 1.8 | 11.0 ± 1.1 | 7.3 ± 0.8$^{a}$ | 8.4 ± 0.9$^{a}$ | 8.9 ± 1.0$^{a}$ | 1 |
| Experiment 2 | 24 | 13.7 ± 1.5 | 4.7 ± 0.9 | 1 | 10.7 ± 1.8 | 8.9 ± 1.4 | 4.5 ± 1.0$^{a}$ | 5.6 ± 1.1$^{ab}$ | 6.6 ± 1.3$^{ab}$ | 2 |
| Experiment 3 | 24 | 15.5 ± 1.9 | 5.3 ± 1.0 | 3 | 12.8 ± 2.2 | 11.1 ± 1.9 | 3.4 ± 0.7$^{b}$ | 5.0 ± 1.0$^{b}$ | 5.6 ± 1.2$^{b}$ | 6 |
| P-value | | 0.9426 | 0.9196 | 0.4233 | 0.5881 | 0.5169 | 0.0031 | 0.0219 | 0.0480 | 0.0595 |
| Treatments | | | | | | | | | | |
| Control | 30 | 13.9 ± 1.2 | 3.7 ± 0.6$^{a}$ | 0 | 11.3 ± 1.5 | 9.7 ± 1.2 | 4.9 ± 0.8 | 6.0 ± 0.8 | 6.7 ± 1.0 | 2 |
| rFSH 60 μg | 42 | 14.8 ± 1.3 | 5.9 ± 0.8$^{b}$ | 5 | 12.8 ± 1.5 | 10.8 ± 1.3 | 5.2 ± 0.7 | 6.8 ± 0.8 | 7.3 ± 0.9 | 7 |
| P-value | | 0.9664 | 0.0224 | 0.0501 | 0.7893 | 0.9184 | 0.9391 | 0.9571 | 0.9840 | 0.2059 |
| Experiment treatment interaction | | 0.8844 | 0.7250 | | 0.7720 | 0.8597 | 0.9385 | 0.9790 | 0.9769 | |

The follicle characteristics from the beginning of treatment until just before artificial insemination are shown in Table 7 and FIGS. 6-9.

Tables 7 shows follicle numbers in superovulation model in nonlactating cows. Follicle development (mean±SEM) was detected by ultrasonography of beef cows treated with 60 μg of rFSH given by single i.m. injection or 300 mg Folltropin®-V given twice daily i.m. injections over 4 days.

TABLE 7

| Treatment | N | Day 0 Follicles 3 to 5 mm | Day 4 Follicles 3 to 5 mm | Day 8 Follicles ≥ 9 mm |
|---|---|---|---|---|
| rFSH | 18 | 13.2 ± 1.1 | 18.9 ± 1.7 | 14.7 ± 2.7 |
| Folltropin-V | 18 | 12.4 ± 1.2 | 17.4 ± 1.3 | 18.4 ± 1.9 |
| P-value | | 0.66 | 0.47 | 0.12 |

vulatory response in the final dosing would appear to be similar to the first two and this will be confirmed following ova/embryo collection. There is concern about the larger number of unovulated (>10 mm) follicles in cows treated with rFSH (mainly due to high number of unovulated follicles in two cows) that needs to be investigated further. More studies are also required to determine the optimal dosage of rFSH to superovulate beef and dairy cows and to determine the long term effects of treating consecutively with rFSH more than three times.

Specificity of Insert for Improved Half-Life

To determine if the observed improved half-life is specific to the sequence of the insert of SEQ ID NO: 1, the human alpha subunit with the insert was modified to remove the amino terminal valine. The two were then tested for their ability to produce cAMP, along with the analog that lacks the insert. The studies showed that the insert is sequence specific and confers superior binding and half-life on the alpha subunit (see FIG. 9). The production conditions were then examined in various growth conditions to optimize for maximal production (see Table 8).

Table 8 shows optimization of production of the human alpha subunit.

| Samples | Average OD | Interpolated ng/ml | Dilution factor | ng/ml * dil | Concentration ng/ml | SEM | Yields ng/dish |
|---|---|---|---|---|---|---|---|
| Insert 1 in GLP Sigma 6 | 1.1753 | 23.10155 | 800 | 18481.24 | 22783.156 | 4301.916 | 2506.1472 |
| medium | 0.92265 | 16.92817 | 1600 | 27085.072 | | | |
| Insert 1 in Excell 302 | 1.1518 | 22.49597 | 800 | 17996.776 | 20802.18 | 2805.404 | 2669.6131 |
| medium | 0.827 | 14.75474 | 1600 | 23607.584 | | | |
| Insert 1 in Lonza | 1.1652 | 22.84037 | 800 | 18272.296 | 22269.612 | 3997.316 | 2820.8175 |
| medium | 0.90043 | 16.41683 | 1600 | 26266.928 | | | |
| Insert 1 in Hyclone | 1.9913 | 24.68149 | 400 | 9872.596 | 12390.186 | 1140.7851 | 1734.6261 |
| medium | 1.37845 | 13.94756 | 800 | 11158.048 | | | |
| | 0.9435 | 8.538053 | 1600 | 13660.885 | | | |
| | 0.57165 | 4.64663 | 3200 | 14869.216 | | | |

Figure 11:
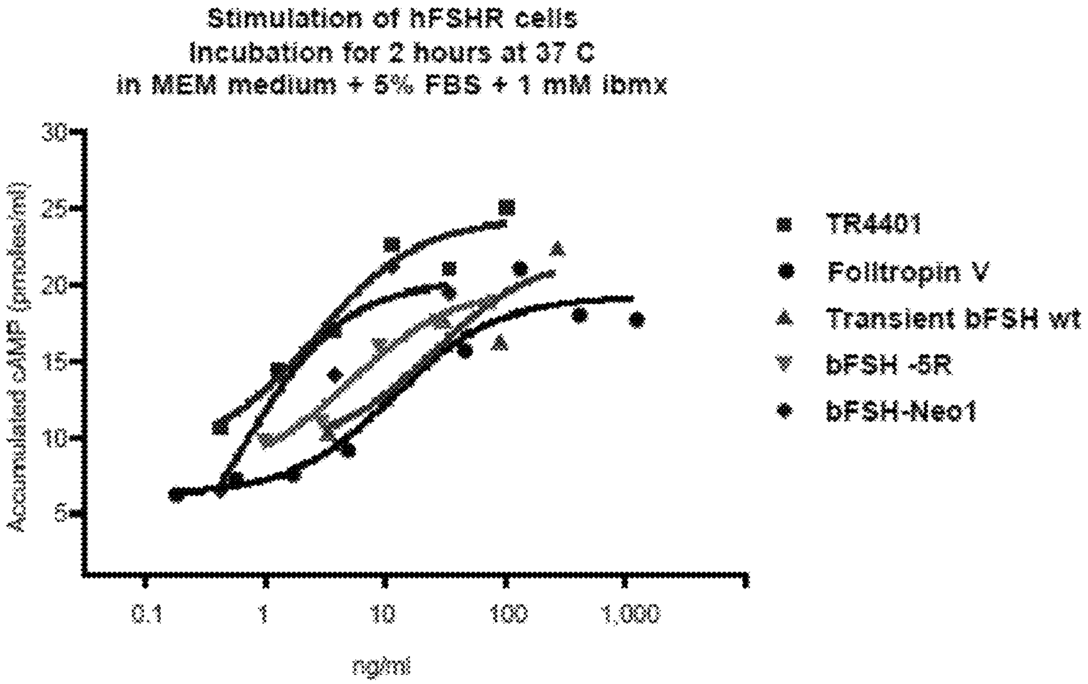
FIG. 11A shows a comparison of cAMP production in response to the human modified alpha subunit with the insert of SEQ ID NO: 1 and the bovine modified alpha subunits that lack the insert.
FIG. 11B shows a comparison of cAMP production in response to the human modified alpha subunit and the bovine subunits with and without various inserts.
Figure 11:
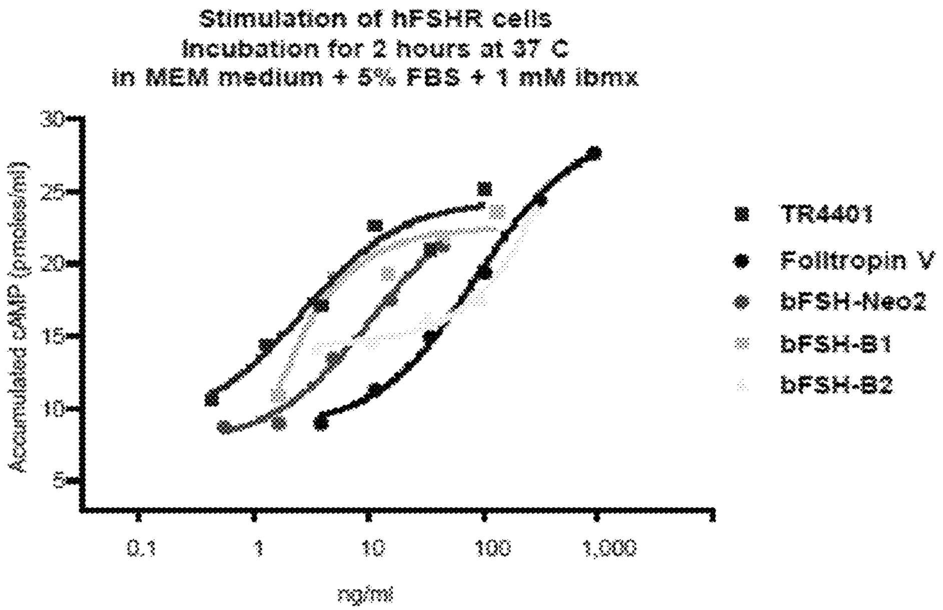

The insert was then examined along with the bovine counterpart and it is confirmed that the increased half-life is specific to the sequence of the insert (see FIG. 11).

What is claimed:

1. A modified bovine follicle-stimulating hormone (FSH) comprising SEQ ID NO: 2 with arginine, histidine, or lysine substitutions at K15, K17, K20, K24 and E18 and an insert of SEQ ID NO: 1 between F6 and T7, wherein the modified bovine FSH has an increased FSH receptor activation compared to bovine wild type FSH.

2. The modified bovine FSH of claim 1, wherein at least one substitution is an arginine substitution.

3. The modified bovine FSH of claim 1, wherein at least one substitution is a histidine substitution.

4. The modified bovine FSH of claim 1, further comprising the beta subunit of a bovine FSH.

5. The modified bovine FSH of claim 4, wherein at least one substitution is an arginine substitution.

6. The modified bovine FSH of claim 5, wherein the substitution at E18 of SEQ ID NO: 2 is an arginine substitution.

7. The modified bovine FSH of claim 1, comprising amino acid substitutions K15R, K17R, E18R, K20R and K24R, and the beta subunit of bovine FSH.

8. The modified bovine FSH of claim 1 comprising an alpha subunit having a sequence of SEQ ID NO: 7.

9. The modified bovine FSH of claim 8, further comprising the beta subunit of bovine FSH.

10. The modified bovine FSH of claim 1, wherein at least one substitution is a lysine substitution.

11. A modified bovine follicle-stimulating hormone (FSH) comprising SEQ ID NO: 2 with substitutions at K15R, K17R, K20R, K24R and E18 and an insert of SEQ ID NO: 1 between F6 and T7 and the beta subunit of bovine FSH, wherein the modified bovine FSH has an increased FSH receptor activation compared to wild type bovine FSH.

12. The modified bovine FSH of claim 11, wherein the alpha subunit comprises SEQ ID NO: 7.

13. The modified bovine FSH of claim 11, where the alpha subunit consists of SEQ ID NO: 7.

14. The modified bovine FSH of claim 1, wherein the modified bovine FSH has a longer half-life and duration of action compared to bovine wild-type FSH.

* * * * *

SEQUENCE LISTING

```
<160> NUMBER OF SEQ ID NOS: 44

<210> SEQ ID NO 1
<211> LENGTH: 6
<212> TYPE: PRT
<213> ORGANISM: Artificial Sequence
<220> FEATURE:
<223> OTHER INFORMATION: Modified glycoprotein insert

<400> SEQUENCE: 1

Asn Val Thr Ile Asn Val
1               5


<210> SEQ ID NO 2
<211> LENGTH: 96
<212> TYPE: PRT
<213> ORGANISM: Bos taurus

<400> SEQUENCE: 2

Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95


<210> SEQ ID NO 3
<211> LENGTH: 96
<212> TYPE: PRT
<213> ORGANISM: Ovis aries

<400> SEQUENCE: 3

Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
            20                  25                  30
```

-continued

```
Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Val Arg Val
65                  70                  75                  80

Glu Asn His Thr Glu Cys His Cys Ser Thr Cys Tyr Tyr His Lys Ser
                85                  90                  95


<210> SEQ ID NO 4
<211> LENGTH: 96
<212> TYPE: PRT
<213> ORGANISM: Equus caballus

<400> SEQUENCE: 4

Phe Pro Asp Gly Glu Phe Thr Thr Gln Asp Cys Pro Glu Cys Lys Leu
1               5                   10                  15

Arg Glu Asn Lys Tyr Phe Phe Lys Leu Gly Val Pro Ile Tyr Gln Cys
            20                  25                  30

Lys Gly Cys Cys Phe Ser Arg Ala Tyr Pro Thr Pro Ala Arg Ser Arg
        35                  40                  45

Lys Thr Met Leu Val Pro Lys Asn Ile Thr Ser Glu Ser Thr Cys Cys
    50                  55                  60

Val Ala Lys Ala Phe Ile Arg Val Thr Val Met Gly Asn Ile Lys Leu
65                  70                  75                  80

Glu Asn His Thr Gln Cys Tyr Cys Ser Thr Cys Tyr His His Lys Ile
                85                  90                  95


<210> SEQ ID NO 5
<211> LENGTH: 96
<212> TYPE: PRT
<213> ORGANISM: Sus scrofa

<400> SEQUENCE: 5

Phe Pro Asp Gly Glu Phe Thr Met Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
        35                  40                  45

Lys Thr Met Leu Val Pro Lys Asn Ile Thr Ser Glu Ala Thr Cys Cys
    50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
                85                  90                  95


<210> SEQ ID NO 6
<211> LENGTH: 92
<212> TYPE: PRT
<213> ORGANISM: Homo sapiens

<400> SEQUENCE: 6

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30
```

-continued

Phe Ser Arg Ala Tyr Pro Thr Pro Leu Arg Ser Lys Lys Thr Met Leu
35 40 45

Val Gln Lys Asn Val Thr Ser Glu Ser Thr Cys Cys Val Ala Lys Ser
50 55 60

Tyr Asn Arg Val Thr Val Met Gly Gly Phe Lys Val Glu Asn His Thr
65 70 75 80

Ala Cys His Cys Ser Thr Cys Tyr Tyr His Lys Ser
85 90

<210> SEQ ID NO 7
<211> LENGTH: 102
<212> TYPE: PRT
<213> ORGANISM: Bos taurus

<400> SEQUENCE: 7

Phe Pro Asp Gly Glu Phe Asn Val Thr Ile Asn Val Thr Met Gln Gly
1 5 10 15

Cys Pro Glu Cys Arg Leu Arg Arg Asn Arg Tyr Phe Ser Arg Pro Asp
20 25 30

Ala Pro Ile Tyr Gln Cys Met Gly Cys Cys Phe Ser Arg Ala Tyr Pro
35 40 45

Thr Pro Ala Arg Ser Lys Lys Thr Met Leu Val Pro Lys Asn Ile Thr
50 55 60

Ser Glu Ala Thr Cys Cys Val Ala Lys Ala Phe Thr Lys Ala Thr Val
65 70 75 80

Met Gly Asn Val Arg Val Glu Asn His Thr Glu Cys His Cys Ser Thr
85 90 95

Cys Tyr Tyr His Lys Ser
100

<210> SEQ ID NO 8
<211> LENGTH: 102
<212> TYPE: PRT
<213> ORGANISM: Ovis aries

<400> SEQUENCE: 8

Phe Pro Asp Gly Glu Phe Asn Val Thr Ile Asn Val Thr Met Gln Gly
1 5 10 15

Cys Pro Glu Cys Arg Leu Arg Arg Asn Arg Tyr Phe Ser Lys Pro Asp
20 25 30

Ala Pro Ile Tyr Gln Cys Met Gly Cys Cys Phe Ser Arg Ala Tyr Pro
35 40 45

Thr Pro Ala Arg Ser Lys Lys Thr Met Leu Val Pro Lys Asn Ile Thr
50 55 60

Ser Glu Ala Thr Cys Cys Val Ala Lys Ala Phe Thr Lys Ala Thr Val
65 70 75 80

Met Gly Asn Val Arg Val Glu Asn His Thr Glu Cys His Cys Ser Thr
85 90 95

Cys Tyr Tyr His Lys Ser
100

<210> SEQ ID NO 9
<211> LENGTH: 102
<212> TYPE: PRT
<213> ORGANISM: Equus caballus

<400> SEQUENCE: 9

Phe Pro Asp Gly Glu Phe Asn Val Thr Ile Asn Val Thr Thr Gln Asp

-continued

```
1               5                   10                  15

Cys Pro Glu Cys Arg Leu Arg Arg Asn Arg Tyr Phe Phe Arg Leu Gly
            20                  25                  30

Val Pro Ile Tyr Gln Cys Lys Gly Cys Cys Phe Ser Arg Ala Tyr Pro
        35                  40                  45

Thr Pro Ala Arg Ser Arg Lys Thr Met Leu Val Pro Lys Asn Ile Thr
    50                  55                  60

Ser Glu Ser Thr Cys Cys Val Ala Lys Ala Phe Ile Arg Val Thr Val
65                  70                  75                  80

Met Gly Asn Ile Lys Leu Glu Asn His Thr Gln Cys Tyr Cys Ser Thr
                85                  90                  95

Cys Tyr His His Lys Ile
            100


<210> SEQ ID NO 10
<211> LENGTH: 102
<212> TYPE: PRT
<213> ORGANISM: Sus scrofa

<400> SEQUENCE: 10

Phe Pro Asp Gly Glu Phe Asn Val Thr Ile Asn Val Thr Met Gln Gly
1               5                   10                  15

Cys Pro Glu Cys Arg Leu Arg Arg Asn Arg Tyr Phe Ser Arg Leu Gly
            20                  25                  30

Ala Pro Ile Tyr Gln Cys Met Gly Cys Cys Phe Ser Arg Ala Tyr Pro
        35                  40                  45

Thr Pro Ala Arg Ser Lys Lys Thr Met Leu Val Pro Lys Asn Ile Thr
    50                  55                  60

Ser Glu Ala Thr Cys Cys Val Ala Lys Ala Phe Thr Lys Ala Thr Val
65                  70                  75                  80

Met Gly Asn Ala Arg Val Glu Asn His Thr Glu Cys His Cys Ser Thr
                85                  90                  95

Cys Tyr Tyr His Lys Ser
            100


<210> SEQ ID NO 11
<211> LENGTH: 99
<212> TYPE: PRT
<213> ORGANISM: Homo sapiens

<400> SEQUENCE: 11

Ala Pro Asp Val Asn Val Thr Ile Asn Val Thr Gln Asp Cys Pro Glu
1               5                   10                  15

Cys Thr Leu Arg Arg Asn Pro Phe Phe Ser Arg Pro Gly Ala Pro Ile
            20                  25                  30

Leu Gln Cys Met Gly Cys Cys Phe Ser Arg Ala Tyr Pro Thr Pro Leu
        35                  40                  45

Arg Ser Lys Lys Thr Met Leu Val Gln Lys Asn Val Thr Ser Glu Ser
    50                  55                  60

Thr Cys Cys Val Ala Lys Ser Tyr Asn Arg Val Thr Val Met Gly Gly
65                  70                  75                  80

Phe Lys Val Glu Asn His Thr Ala Cys His Cys Ser Thr Cys Tyr Tyr
                85                  90                  95

His Lys Ser


<210> SEQ ID NO 12
```

-continued

<211> LENGTH: 7
<212> TYPE: PRT
<213> ORGANISM: Artificial Sequence
<220> FEATURE:
<223> OTHER INFORMATION: Modified glycoprotein insert

<400> SEQUENCE: 12

```
Thr Asn Val Thr Ile Asn Val
1               5
```

<210> SEQ ID NO 13
<211> LENGTH: 92
<212> TYPE: PRT
<213> ORGANISM: Homo sapiens

<400> SEQUENCE: 13

```
Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90
```

<210> SEQ ID NO 14
<211> LENGTH: 102
<212> TYPE: PRT
<213> ORGANISM: Bos taurus

<400> SEQUENCE: 14

```
Phe Pro Asp Gly Glu Phe Asn Val Thr Ile Asn Val Thr Met Gln Gly
1               5                   10                  15

Cys Pro Glu Cys Lys Leu Lys Arg Asn Lys Tyr Phe Ser Lys Pro Asp
            20                  25                  30

Ala Pro Ile Tyr Gln Cys Met Gly Cys Cys Phe Ser Arg Ala Tyr Pro
        35                  40                  45

Thr Pro Ala Arg Ser Lys Lys Thr Met Leu Val Pro Lys Asn Ile Thr
    50                  55                  60

Ser Glu Ala Thr Cys Cys Val Ala Lys Ala Phe Thr Lys Ala Thr Val
65                  70                  75                  80

Met Gly Asn Val Arg Val Glu Asn His Thr Glu Cys His Cys Ser Thr
                85                  90                  95

Cys Tyr Tyr His Lys Ser
            100
```

<210> SEQ ID NO 15
<211> LENGTH: 103
<212> TYPE: PRT
<213> ORGANISM: Bos taurus

<400> SEQUENCE: 15

```
Phe Pro Asp Gly Glu Phe Thr Asn Val Thr Ile Asn Val Thr Met Gln
1               5                   10                  15

Gly Cys Pro Glu Cys Arg Leu Arg Arg Asn Arg Tyr Phe Ser Arg Pro
            20                  25                  30
```

-continued

```
Asp Ala Pro Ile Tyr Gln Cys Met Gly Cys Cys Phe Ser Arg Ala Tyr
        35                  40                  45

Pro Thr Pro Ala Arg Ser Lys Lys Thr Met Leu Val Pro Lys Asn Ile
    50                  55                  60

Thr Ser Glu Ala Thr Cys Cys Val Ala Lys Ala Phe Thr Lys Ala Thr
65                  70                  75                  80

Val Met Gly Asn Val Arg Val Glu Asn His Thr Glu Cys His Cys Ser
                85                  90                  95

Thr Cys Tyr Tyr His Lys Ser
            100


<210> SEQ ID NO 16
<211> LENGTH: 103
<212> TYPE: PRT
<213> ORGANISM: Bos taurus

<400> SEQUENCE: 16

Phe Pro Asp Gly Glu Phe Thr Asn Val Thr Ile Asn Val Thr Met Gln
1               5                   10                  15

Gly Cys Pro Glu Cys Lys Leu Lys Arg Asn Lys Tyr Phe Ser Lys Pro
            20                  25                  30

Asp Ala Pro Ile Tyr Gln Cys Met Gly Cys Cys Phe Ser Arg Ala Tyr
        35                  40                  45

Pro Thr Pro Ala Arg Ser Lys Lys Thr Met Leu Val Pro Lys Asn Ile
    50                  55                  60

Thr Ser Glu Ala Thr Cys Cys Val Ala Lys Ala Phe Thr Lys Ala Thr
65                  70                  75                  80

Val Met Gly Asn Val Arg Val Glu Asn His Thr Glu Cys His Cys Ser
                85                  90                  95

Thr Cys Tyr Tyr His Lys Ser
            100


<210> SEQ ID NO 17
<211> LENGTH: 98
<212> TYPE: PRT
<213> ORGANISM: Bos taurus

<400> SEQUENCE: 17

Phe Pro Asp Gly Glu Phe Asn Val Thr Met Gln Gly Cys Pro Glu Cys
1               5                   10                  15

Arg Leu Arg Arg Asn Arg Tyr Phe Ser Arg Pro Asp Ala Pro Ile Tyr
            20                  25                  30

Gln Cys Met Gly Cys Cys Phe Ser Arg Ala Tyr Pro Thr Pro Ala Arg
        35                  40                  45

Ser Lys Lys Thr Met Leu Val Pro Lys Asn Ile Thr Ser Glu Ala Thr
    50                  55                  60

Cys Cys Val Ala Lys Ala Phe Thr Lys Ala Thr Val Met Gly Asn Val
65                  70                  75                  80

Arg Val Glu Asn His Thr Glu Cys His Cys Ser Thr Cys Tyr Tyr His
                85                  90                  95

Lys Ser


<210> SEQ ID NO 18
<211> LENGTH: 98
<212> TYPE: PRT
<213> ORGANISM: Bos taurus
```

-continued

<400> SEQUENCE: 18

Phe Pro Asp Gly Glu Phe Asn Val Thr Met Gln Gly Cys Pro Glu Cys
1 5 10 15

Lys Leu Lys Arg Asn Lys Tyr Phe Ser Lys Pro Asp Ala Pro Ile Tyr
20 25 30

Gln Cys Met Gly Cys Cys Phe Ser Arg Ala Tyr Pro Thr Pro Ala Arg
35 40 45

Ser Lys Lys Thr Met Leu Val Pro Lys Asn Ile Thr Ser Glu Ala Thr
50 55 60

Cys Cys Val Ala Lys Ala Phe Thr Lys Ala Thr Val Met Gly Asn Val
65 70 75 80

Arg Val Glu Asn His Thr Glu Cys His Cys Ser Thr Cys Tyr Tyr His
85 90 95

Lys Ser

<210> SEQ ID NO 19
<211> LENGTH: 99
<212> TYPE: PRT
<213> ORGANISM: Bos taurus

<400> SEQUENCE: 19

Phe Pro Asp Gly Glu Phe Thr Asn Val Thr Met Gln Gly Cys Pro Glu
1 5 10 15

Cys Lys Leu Lys Arg Asn Lys Tyr Phe Ser Lys Pro Asp Ala Pro Ile
20 25 30

Tyr Gln Cys Met Gly Cys Cys Phe Ser Arg Ala Tyr Pro Thr Pro Ala
35 40 45

Arg Ser Lys Lys Thr Met Leu Val Pro Lys Asn Ile Thr Ser Glu Ala
50 55 60

Thr Cys Cys Val Ala Lys Ala Phe Thr Lys Ala Thr Val Met Gly Asn
65 70 75 80

Val Arg Val Glu Asn His Thr Glu Cys His Cys Ser Thr Cys Tyr Tyr
85 90 95

His Lys Ser

<210> SEQ ID NO 20
<211> LENGTH: 8
<212> TYPE: PRT
<213> ORGANISM: Artificial Sequence
<220> FEATURE:
<223> OTHER INFORMATION: Modified glycoprotein insert

<400> SEQUENCE: 20

Val Asn Val Thr Ile Asn Val Thr
1 5

<210> SEQ ID NO 21
<211> LENGTH: 99
<212> TYPE: PRT
<213> ORGANISM: Homo sapiens

<400> SEQUENCE: 21

Ala Pro Asp Asn Val Thr Ile Asn Val Thr Gln Asp Cys Pro Glu Cys
1 5 10 15

Cys Thr Leu Arg Arg Asn Pro Phe Phe Ser Arg Pro Gly Ala Pro Ile
20 25 30

Leu Gln Cys Met Gly Cys Cys Phe Ser Arg Ala Tyr Pro Thr Pro Leu
35 40 45

```
Arg Ser Lys Lys Thr Met Leu Val Gln Lys Asn Val Thr Ser Glu Ser
    50                  55                  60

Thr Cys Cys Val Ala Lys Ser Tyr Asn Arg Val Thr Val Met Gly Gly
65                  70                  75                  80

Phe Lys Val Glu Asn His Thr Ala Cys His Cys Ser Thr Cys Tyr Tyr
                85                  90                  95

His Lys Ser


<210> SEQ ID NO 22
<211> LENGTH: 99
<212> TYPE: PRT
<213> ORGANISM: Bos taurus

<400> SEQUENCE: 22

Phe Pro Asp Gly Glu Phe Thr Asn Val Thr Met Gln Gly Cys Pro Glu
1               5                   10                  15

Cys Arg Leu Arg Arg Asn Arg Tyr Phe Ser Arg Pro Asp Ala Pro Ile
            20                  25                  30

Tyr Gln Cys Met Gly Cys Cys Phe Ser Arg Ala Tyr Pro Thr Pro Ala
        35                  40                  45

Arg Ser Lys Lys Thr Met Leu Val Pro Lys Asn Ile Thr Ser Glu Ala
    50                  55                  60

Thr Cys Cys Val Ala Lys Ala Phe Thr Lys Ala Thr Val Met Gly Asn
65                  70                  75                  80

Val Arg Val Glu Asn His Thr Glu Cys His Cys Ser Thr Cys Tyr Tyr
                85                  90                  95

His Lys Ser


<210> SEQ ID NO 23
<211> LENGTH: 32
<212> TYPE: PRT
<213> ORGANISM: Artificial Sequence
<220> FEATURE:
<223> OTHER INFORMATION: bFSH superagonist (5R)

<400> SEQUENCE: 23

Phe Pro Asp Gly Glu Phe Thr Met Gln Gly Cys Pro Glu Cys Arg Leu
1               5                   10                  15

Arg Arg Asn Arg Tyr Phe Ser Arg Pro Asp Ala Pro Ile Tyr Gln Cys
            20                  25                  30


<210> SEQ ID NO 24
<211> LENGTH: 32
<212> TYPE: PRT
<213> ORGANISM: Artificial Sequence
<220> FEATURE:
<223> OTHER INFORMATION: bFSH superagonist (4R+1K)

<400> SEQUENCE: 24

Phe Pro Asp Gly Glu Phe Thr Met Gln Gly Cys Pro Glu Cys Arg Leu
1               5                   10                  15

Arg Lys Asn Arg Tyr Phe Ser Arg Pro Asp Ala Pro Ile Tyr Gln Cys
            20                  25                  30


<210> SEQ ID NO 25
<211> LENGTH: 38
<212> TYPE: PRT
<213> ORGANISM: Artificial Sequence
<220> FEATURE:
<223> OTHER INFORMATION: bFSH superagonist (5R+Ins1)
```

<400> SEQUENCE: 25

```
Phe Pro Asp Gly Glu Phe Asn Val Thr Ile Asn Val Thr Met Gln Gly
1               5                   10                  15

Cys Pro Glu Cys Arg Leu Arg Arg Asn Arg Tyr Phe Ser Arg Pro Asp
            20                  25                  30

Ala Pro Ile Tyr Gln Cys
        35
```

<210> SEQ ID NO 26
<211> LENGTH: 39
<212> TYPE: PRT
<213> ORGANISM: Artificial Sequence
<220> FEATURE:
<223> OTHER INFORMATION: bFSH superagonist (5R+Ins2)

<400> SEQUENCE: 26

```
Phe Pro Asp Gly Glu Phe Thr Asn Val Thr Ile Asn Val Thr Met Gln
1               5                   10                  15

Gly Cys Pro Glu Cys Arg Leu Arg Arg Asn Arg Tyr Phe Ser Arg Pro
            20                  25                  30

Asp Ala Pro Ile Tyr Gln Cys
        35
```

<210> SEQ ID NO 27
<211> LENGTH: 34
<212> TYPE: PRT
<213> ORGANISM: Artificial Sequence
<220> FEATURE:
<223> OTHER INFORMATION: bFSH superagonist (5R+Ins3)

<400> SEQUENCE: 27

```
Phe Pro Asp Gly Glu Phe Asn Val Thr Met Gln Gly Cys Pro Glu Cys
1               5                   10                  15

Arg Leu Arg Arg Asn Arg Tyr Phe Ser Arg Pro Asp Ala Pro Ile Tyr
            20                  25                  30

Gln Cys
```

<210> SEQ ID NO 28
<211> LENGTH: 35
<212> TYPE: PRT
<213> ORGANISM: Artificial Sequence
<220> FEATURE:
<223> OTHER INFORMATION: bFSH superagonist (5R+Ins4)

<400> SEQUENCE: 28

```
Phe Pro Asp Gly Glu Phe Thr Asn Val Thr Met Gln Gly Cys Pro Glu
1               5                   10                  15

Cys Arg Leu Arg Arg Asn Arg Tyr Phe Ser Arg Pro Asp Ala Pro Ile
            20                  25                  30

Tyr Gln Cys
        35
```

<210> SEQ ID NO 29
<211> LENGTH: 38
<212> TYPE: PRT
<213> ORGANISM: Artificial Sequence
<220> FEATURE:
<223> OTHER INFORMATION: bFSH superagonist (4R+1K+Ins1)

<400> SEQUENCE: 29

```
Phe Pro Asp Gly Glu Phe Asn Val Thr Ile Asn Val Thr Met Gln Gly
```

```
1               5                   10                  15

Cys Pro Glu Cys Arg Leu Arg Lys Asn Arg Tyr Phe Ser Arg Pro Asp
            20                  25                  30

Ala Pro Ile Tyr Gln Cys
        35


<210> SEQ ID NO 30
<211> LENGTH: 39
<212> TYPE: PRT
<213> ORGANISM: Artificial Sequence
<220> FEATURE:
<223> OTHER INFORMATION: bFSH superagonist (4R+1K+Ins2)

<400> SEQUENCE: 30

Phe Pro Asp Gly Glu Phe Thr Asn Val Thr Ile Asn Val Thr Met Gln
1               5                   10                  15

Gly Cys Pro Glu Cys Arg Leu Arg Lys Asn Arg Tyr Phe Ser Arg Pro
            20                  25                  30

Asp Ala Pro Ile Tyr Gln Cys
        35


<210> SEQ ID NO 31
<211> LENGTH: 34
<212> TYPE: PRT
<213> ORGANISM: Artificial Sequence
<220> FEATURE:
<223> OTHER INFORMATION: bFSH superagonist (4R+1K+Ins3)

<400> SEQUENCE: 31

Phe Pro Asp Gly Glu Phe Asn Val Thr Met Gln Gly Cys Pro Glu Cys
1               5                   10                  15

Arg Leu Arg Lys Asn Arg Tyr Phe Ser Arg Pro Asp Ala Pro Ile Tyr
            20                  25                  30

Gln Cys


<210> SEQ ID NO 32
<211> LENGTH: 35
<212> TYPE: PRT
<213> ORGANISM: Artificial Sequence
<220> FEATURE:
<223> OTHER INFORMATION: bFSH superagonist (4R+1K+Ins4)

<400> SEQUENCE: 32

Phe Pro Asp Gly Glu Phe Thr Asn Val Thr Met Gln Gly Cys Pro Glu
1               5                   10                  15

Cys Arg Leu Arg Lys Asn Arg Tyr Phe Ser Arg Pro Asp Ala Pro Ile
            20                  25                  30

Tyr Gln Cys
        35


<210> SEQ ID NO 33
<211> LENGTH: 29
<212> TYPE: PRT
<213> ORGANISM: Artificial Sequence
<220> FEATURE:
<223> OTHER INFORMATION: hFSH superagonist (4R)

<400> SEQUENCE: 33

Ala Pro Asp Val Gln Asp Cys Pro Glu Cys Cys Thr Leu Arg Arg Asn
1               5                   10                  15

Arg Phe Phe Ser Arg Pro Gly Ala Pro Ile Leu Gln Cys
            20                  25
```

-continued

<210> SEQ ID NO 34
<211> LENGTH: 36
<212> TYPE: PRT
<213> ORGANISM: Artificial Sequence
<220> FEATURE:
<223> OTHER INFORMATION: hFSH superagonist (4R+Ins1)

<400> SEQUENCE: 34

Ala Pro Asp Val Asn Val Thr Ile Asn Val Thr Gln Asp Cys Pro Glu
1 5 10 15

Cys Cys Thr Leu Arg Arg Asn Arg Phe Phe Ser Arg Pro Gly Ala Pro
20 25 30

Ile Leu Gln Cys
35

<210> SEQ ID NO 35
<211> LENGTH: 35
<212> TYPE: PRT
<213> ORGANISM: Artificial Sequence
<220> FEATURE:
<223> OTHER INFORMATION: hFSH superagonist (4R+Ins2)

<400> SEQUENCE: 35

Ala Pro Asp Asn Val Thr Ile Asn Val Thr Gln Asp Cys Pro Glu Cys
1 5 10 15

Cys Thr Leu Arg Arg Asn Arg Phe Phe Ser Arg Pro Gly Ala Pro Ile
20 25 30

Leu Gln Cys
35

<210> SEQ ID NO 36
<211> LENGTH: 31
<212> TYPE: PRT
<213> ORGANISM: Artificial Sequence
<220> FEATURE:
<223> OTHER INFORMATION: hFSH superagonist (4R+Ins3)

<400> SEQUENCE: 36

Ala Pro Asp Asn Val Thr Gln Asp Cys Pro Glu Cys Cys Thr Leu Arg
1 5 10 15

Arg Asn Arg Phe Phe Ser Arg Pro Gly Ala Pro Ile Leu Gln Cys
20 25 30

<210> SEQ ID NO 37
<211> LENGTH: 32
<212> TYPE: PRT
<213> ORGANISM: Artificial Sequence
<220> FEATURE:
<223> OTHER INFORMATION: hFSH superagonist (4R+Ins4)

<400> SEQUENCE: 37

Ala Pro Asp Val Asn Val Thr Gln Asp Cys Pro Glu Cys Cys Thr Leu
1 5 10 15

Arg Arg Asn Arg Phe Phe Ser Arg Pro Gly Ala Pro Ile Leu Gln Cys
20 25 30

<210> SEQ ID NO 38
<211> LENGTH: 101
<212> TYPE: PRT
<213> ORGANISM: Equus caballus

<400> SEQUENCE: 38

-continued

```
Phe Pro Asp Gly Glu Phe Asn Val Thr Ile Asn Val Thr Gln Asp Cys
1               5                   10                  15

Pro Glu Cys Arg Leu Arg Arg Asn Arg Tyr Phe Phe Arg Leu Gly Val
            20                  25                  30

Pro Ile Tyr Gln Cys Lys Gly Cys Cys Phe Ser Arg Ala Tyr Pro Thr
        35                  40                  45

Pro Ala Arg Ser Arg Lys Thr Met Leu Val Pro Lys Asn Ile Thr Ser
    50                  55                  60

Glu Ser Thr Cys Cys Val Ala Lys Ala Phe Ile Arg Val Thr Val Met
65                  70                  75                  80

Gly Asn Ile Lys Leu Glu Asn His Thr Gln Cys Tyr Cys Ser Thr Cys
                85                  90                  95

Tyr His His Lys Ile
            100


<210> SEQ ID NO 39
<211> LENGTH: 101
<212> TYPE: PRT
<213> ORGANISM: Equus caballus

<400> SEQUENCE: 39

Phe Pro Asp Gly Glu Phe Asn Val Thr Ile Asn Val Thr Gln Asp Cys
1               5                   10                  15

Pro Glu Cys Arg Leu Arg Lys Asn Arg Tyr Phe Phe Arg Leu Gly Val
            20                  25                  30

Pro Ile Tyr Gln Cys Lys Gly Cys Cys Phe Ser Arg Ala Tyr Pro Thr
        35                  40                  45

Pro Ala Arg Ser Arg Lys Thr Met Leu Val Pro Lys Asn Ile Thr Ser
    50                  55                  60

Glu Ser Thr Cys Cys Val Ala Lys Ala Phe Ile Arg Val Thr Val Met
65                  70                  75                  80

Gly Asn Ile Lys Leu Glu Asn His Thr Gln Cys Tyr Cys Ser Thr Cys
                85                  90                  95

Tyr His His Lys Ile
            100


<210> SEQ ID NO 40
<211> LENGTH: 102
<212> TYPE: PRT
<213> ORGANISM: Equus caballus

<400> SEQUENCE: 40

Phe Pro Asp Gly Glu Phe Asn Val Thr Ile Asn Val Thr Thr Gln Asp
1               5                   10                  15

Cys Pro Glu Cys Arg Leu Arg Lys Asn Arg Tyr Phe Phe Arg Leu Gly
            20                  25                  30

Val Pro Ile Tyr Gln Cys Lys Gly Cys Cys Phe Ser Arg Ala Tyr Pro
        35                  40                  45

Thr Pro Ala Arg Ser Arg Lys Thr Met Leu Val Pro Lys Asn Ile Thr
    50                  55                  60

Ser Glu Ser Thr Cys Cys Val Ala Lys Ala Phe Ile Arg Val Thr Val
65                  70                  75                  80

Met Gly Asn Ile Lys Leu Glu Asn His Thr Gln Cys Tyr Cys Ser Thr
                85                  90                  95

Cys Tyr His His Lys Ile
            100
```

<210> SEQ ID NO 41
<211> LENGTH: 101
<212> TYPE: PRT
<213> ORGANISM: Equus caballus

<400> SEQUENCE: 41

```
Phe Pro Asp Gly Glu Phe Asn Val Thr Ile Asn Val Thr Gln Asp Cys
1               5                   10                  15

Pro Glu Cys Arg Leu Arg His Asn Arg Tyr Phe Phe Arg Leu Gly Val
            20                  25                  30

Pro Ile Tyr Gln Cys Lys Gly Cys Cys Phe Ser Arg Ala Tyr Pro Thr
        35                  40                  45

Pro Ala Arg Ser Arg Lys Thr Met Leu Val Pro Lys Asn Ile Thr Ser
    50                  55                  60

Glu Ser Thr Cys Cys Val Ala Lys Ala Phe Ile Arg Val Thr Val Met
65                  70                  75                  80

Gly Asn Ile Lys Leu Glu Asn His Thr Gln Cys Tyr Cys Ser Thr Cys
                85                  90                  95

Tyr His His Lys Ile
            100
```

<210> SEQ ID NO 42
<211> LENGTH: 102
<212> TYPE: PRT
<213> ORGANISM: Equus caballus

<400> SEQUENCE: 42

```
Phe Pro Asp Gly Glu Phe Asn Val Thr Ile Asn Val Thr Thr Gln Asp
1               5                   10                  15

Cys Pro Glu Cys Arg Leu Arg His Asn Arg Tyr Phe Phe Arg Leu Gly
            20                  25                  30

Val Pro Ile Tyr Gln Cys Lys Gly Cys Cys Phe Ser Arg Ala Tyr Pro
        35                  40                  45

Thr Pro Ala Arg Ser Arg Lys Thr Met Leu Val Pro Lys Asn Ile Thr
    50                  55                  60

Ser Glu Ser Thr Cys Cys Val Ala Lys Ala Phe Ile Arg Val Thr Val
65                  70                  75                  80

Met Gly Asn Ile Lys Leu Glu Asn His Thr Gln Cys Tyr Cys Ser Thr
                85                  90                  95

Cys Tyr His His Lys Ile
            100
```

<210> SEQ ID NO 43
<211> LENGTH: 28
<212> TYPE: PRT
<213> ORGANISM: Equus caballus

<400> SEQUENCE: 43

```
Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys
            20                  25
```

-continued

```
<210> SEQ ID NO 44
<211> LENGTH: 32
<212> TYPE: PRT
<213> ORGANISM: Equus caballus

<400> SEQUENCE: 44

Phe Pro Asp Gly Glu Phe Thr Met Gln Gly Cys Pro Glu Cys Lys Leu
1               5                   10                  15

Lys Glu Asn Lys Tyr Phe Ser Lys Pro Asp Ala Pro Ile Tyr Gln Cys
            20                  25                  30
```